(12) United States Patent
Cabiri

(10) Patent No.: US 9,393,365 B2
(45) Date of Patent: *Jul. 19, 2016

(54) FAIL SAFE POINT PROTECTOR FOR NEEDLE SAFETY FLAP

(71) Applicant: MEDIMOP Medical Projects Ltd., Ra'anana (IL)

(72) Inventor: Oz Cabiri, Macabim-Reut (IL)

(73) Assignee: Medimop Medical Projects Ltd., Ra'anana (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/715,791

(22) Filed: May 19, 2015

(65) Prior Publication Data

US 2015/0250946 A1    Sep. 10, 2015

Related U.S. Application Data

(63) Continuation of application No. 13/429,840, filed on Mar. 26, 2012, now Pat. No. 9,072,827.

(51) Int. Cl.
*A61M 5/162* (2006.01)
*A61M 5/32* (2006.01)
(Continued)

(52) U.S. Cl.
CPC .......... *A61M 5/1626* (2013.01); *A61M 5/14244* (2013.01); *A61M 5/158* (2013.01); *A61M 5/3275* (2013.01)

(58) Field of Classification Search
CPC ............ A61M 5/1626; A61M 5/3275; A61M 5/14244; A61M 5/158; A61M 2209/045; A61M 2005/1581; A61M 2005/3249; A61M 39/0208

USPC ......... 604/110, 93.01, 116, 117, 162, 164.01, 604/164.04, 164.07, 164.08, 165.01, 604/165.02, 165.03, 165.04, 167.01, 171, 604/174, 177, 178, 181, 187, 191, 192, 197, 604/198, 263, 264, 272

See application file for complete search history.

(56) References Cited

U.S. PATENT DOCUMENTS

| 1,795,630 | A | 3/1931 | Wilson |
| 2,860,635 | A | 11/1958 | Wilburn |

(Continued)

FOREIGN PATENT DOCUMENTS

| CN | 1747683 A | 3/2006 |
| CN | 1863566 A | 11/2006 |

(Continued)

OTHER PUBLICATIONS

Int'l Preliminary Report on Patentability issued May 14, 2015 in Int'l Application No. PCT/US2013/065211.

(Continued)

*Primary Examiner* — Manuel Mendez
(74) *Attorney, Agent, or Firm* — Panitch Schwarze Belisario & Nadel LLP

(57) ABSTRACT

A method and device are disclosed for preventing a needle stick hazard in the event of a collapse of a protective needle flap of a portable drug pump. The device may include a needle guide, a secure space and/or a shield. A point of a needle is optionally deflected into a secure space upon collapse of the protective flap. The space may optionally be shielded. Optionally, the support linking the needle to the pump may pivot and/or translate. Optionally, there may be an exposing position wherein the needle protrudes through an opening in the flap. Optionally, the opening may be non-circular.

9 Claims, 16 Drawing Sheets

(51) Int. Cl.
*A61M 5/158* (2006.01)
*A61M 5/142* (2006.01)

(56) References Cited

U.S. PATENT DOCUMENTS

| | | | |
|---|---|---|---|
| 3,203,269 A | 8/1965 | Perrine |
| 3,212,685 A | 10/1965 | Swan et al. |
| 3,794,028 A | 2/1974 | Mueller et al. |
| 3,994,295 A | 11/1976 | Wulff |
| 4,195,636 A | 4/1980 | Behnke |
| 4,218,724 A | 8/1980 | Kaufman |
| 4,273,122 A | 6/1981 | Whitney et al. |
| 4,300,554 A | 11/1981 | Hessberg et al. |
| 4,403,987 A | 9/1983 | Gottinger |
| 4,435,173 A | 3/1984 | Siposs et al. |
| 4,465,478 A | 8/1984 | Sabelman et al. |
| 4,565,543 A | 1/1986 | Bekkering et al. |
| 4,585,439 A | 4/1986 | Michel |
| 4,599,082 A | 7/1986 | Grimard |
| 4,601,702 A | 7/1986 | Hudson |
| 4,685,903 A | 8/1987 | Cable et al. |
| 4,698,055 A | 10/1987 | Sealfon |
| 4,810,215 A | 3/1989 | Kaneko |
| 4,850,966 A | 7/1989 | Grau et al. |
| 4,867,743 A | 9/1989 | Vaillancourt |
| 4,886,499 A | 12/1989 | Cirelli et al. |
| 4,919,596 A | 4/1990 | Slate et al. |
| 4,929,241 A | 5/1990 | Kulli |
| 4,950,246 A | 8/1990 | Muller |
| D322,671 S | 12/1991 | Szwarc |
| 5,109,850 A | 5/1992 | Blanco et al. |
| 5,112,317 A | 5/1992 | Michel |
| 5,131,816 A | 7/1992 | Brown et al. |
| 5,190,521 A | 3/1993 | Hubbard et al. |
| 5,254,096 A | 10/1993 | Rondelet et al. |
| 5,300,045 A | 4/1994 | Plassche, Jr. |
| 5,342,313 A | 8/1994 | Campbell et al. |
| 5,348,544 A | 9/1994 | Sweeney et al. |
| 5,366,498 A | 11/1994 | Brannan et al. |
| 5,383,865 A | 1/1995 | Michel |
| 5,478,315 A | 12/1995 | Brothers et al. |
| 5,482,446 A | 1/1996 | Williamson et al. |
| 5,496,274 A | 3/1996 | Graves et al. |
| 5,501,665 A | 3/1996 | Jhuboo et al. |
| 5,505,709 A | 4/1996 | Funderburk et al. |
| 5,562,686 A | 10/1996 | Sauer et al. |
| 5,593,390 A | 1/1997 | Castellano et al. |
| 5,616,132 A | 4/1997 | Newman |
| 5,643,218 A | 7/1997 | Lynn et al. |
| 5,645,955 A | 7/1997 | Maglica |
| 5,647,853 A | 7/1997 | Feldmann et al. |
| 5,662,678 A | 9/1997 | Macklin |
| 5,672,160 A | 9/1997 | Osterlind et al. |
| 5,690,618 A | 11/1997 | Smith et al. |
| D393,314 S | 4/1998 | Meisner et al. |
| 5,766,186 A | 6/1998 | Faraz et al. |
| 5,795,675 A | 8/1998 | Maglica |
| 5,800,420 A | 9/1998 | Gross et al. |
| 5,807,375 A | 9/1998 | Gross et al. |
| 5,814,020 A | 9/1998 | Gross |
| 5,836,920 A | 11/1998 | Robertson |
| 5,848,991 A | 12/1998 | Gross et al. |
| 5,851,197 A | 12/1998 | Marano et al. |
| 5,858,001 A | 1/1999 | Tsals et al. |
| 5,858,008 A | 1/1999 | Capaccio |
| 5,868,710 A | 2/1999 | Battiato et al. |
| 5,931,814 A | 8/1999 | Alex et al. |
| 5,941,850 A | 8/1999 | Shah et al. |
| 5,948,392 A | 9/1999 | Haslwanter et al. |
| 5,954,697 A | 9/1999 | Srisathapat et al. |
| 5,957,895 A | 9/1999 | Sage et al. |
| 5,968,011 A | 10/1999 | Larsen et al. |
| 5,993,423 A | 11/1999 | Choi |
| 6,004,297 A | 12/1999 | Steenfeldt-Jensen et al. |
| 6,033,245 A | 3/2000 | Yamkovoy |
| 6,033,377 A | 3/2000 | Rasmussen et al. |
| 6,064,797 A | 5/2000 | Crittendon et al. |
| 6,074,369 A | 6/2000 | Sage et al. |
| 6,186,982 B1 | 2/2001 | Gross et al. |
| 6,200,289 B1 | 3/2001 | Hochman et al. |
| 6,200,296 B1 | 3/2001 | Dibiasi et al. |
| 6,224,569 B1 | 5/2001 | Brimhall |
| 6,248,093 B1 | 6/2001 | Moberg |
| 6,277,095 B1 | 8/2001 | Kriesel et al. |
| 6,277,098 B1 | 8/2001 | Klitmose et al. |
| 6,277,099 B1 | 8/2001 | Strowe et al. |
| 6,287,283 B1 | 9/2001 | Ljunggreen et al. |
| 6,293,925 B1 | 9/2001 | Safabash et al. |
| 6,302,633 B1 | 10/2001 | Poe |
| 6,336,729 B1 | 1/2002 | Pavelle et al. |
| 6,345,968 B1 | 2/2002 | Shupe |
| 6,377,848 B1 | 4/2002 | Garde et al. |
| 6,391,005 B1 | 5/2002 | Lum et al. |
| 6,423,029 B1 | 7/2002 | Elsberry |
| D465,026 S | 10/2002 | May et al. |
| 6,458,102 B1 | 10/2002 | Mann et al. |
| 6,485,461 B1 | 11/2002 | Mason et al. |
| 6,485,465 B2 | 11/2002 | Moberg et al. |
| 6,500,150 B1 | 12/2002 | Gross et al. |
| 6,503,231 B1 | 1/2003 | Prausnitz et al. |
| 6,511,336 B1 | 1/2003 | Turek et al. |
| 6,517,517 B1 | 2/2003 | Farrugia et al. |
| D471,274 S | 3/2003 | Diaz et al. |
| D471,983 S | 3/2003 | Hippolyte et al. |
| 6,558,351 B1 | 5/2003 | Steil et al. |
| 6,589,229 B1 | 7/2003 | Connelly et al. |
| 6,595,956 B1 | 7/2003 | Gross et al. |
| 6,595,960 B2 | 7/2003 | West et al. |
| 6,645,181 B1 | 11/2003 | Lavi et al. |
| 6,652,482 B2 | 11/2003 | Hochman |
| 6,656,158 B2 | 12/2003 | Mahoney et al. |
| 6,656,159 B2 | 12/2003 | Flaherty |
| 6,659,980 B2 | 12/2003 | Moberg et al. |
| 6,673,033 B1 | 1/2004 | Sciulli et al. |
| 6,679,862 B2 | 1/2004 | Diaz et al. |
| 6,689,118 B2 | 2/2004 | Alchas et al. |
| 6,699,218 B2 | 3/2004 | Flaherty et al. |
| 6,722,916 B2 | 4/2004 | Buccinna et al. |
| 6,743,211 B1 | 6/2004 | Prausnitz et al. |
| 6,749,587 B2 | 6/2004 | Flaherty |
| 6,752,787 B1 | 6/2004 | Causey, III et al. |
| 6,768,425 B2 | 7/2004 | Flaherty et al. |
| 6,786,890 B2 | 9/2004 | Preuthun et al. |
| 6,800,071 B1 | 10/2004 | McConnell et al. |
| 6,805,687 B2 | 10/2004 | Dextradeur et al. |
| 6,824,529 B2 | 11/2004 | Gross et al. |
| 6,843,782 B2 | 1/2005 | Gross et al. |
| 6,854,620 B2 | 2/2005 | Ramey |
| 6,905,298 B1 | 6/2005 | Haring |
| 6,908,452 B2 | 6/2005 | Diaz et al. |
| 6,960,192 B1 | 11/2005 | Flaherty et al. |
| 6,972,002 B2 | 12/2005 | Thorne |
| 6,997,727 B1 | 2/2006 | Legrady et al. |
| 7,001,360 B2 | 2/2006 | Veasey et al. |
| 7,034,223 B2 | 4/2006 | Fan et al. |
| 7,048,715 B2 | 5/2006 | Diaz et al. |
| 7,060,054 B2 | 6/2006 | Nissels |
| 7,060,059 B2 | 6/2006 | Keith et al. |
| 7,097,637 B2 | 8/2006 | Triplett et al. |
| 7,128,727 B2 | 10/2006 | Flaherty et al. |
| 7,144,384 B2 | 12/2006 | Gorman et al. |
| D544,092 S | 6/2007 | Lewis |
| 7,225,694 B2 | 6/2007 | Said |
| 7,247,149 B2 | 7/2007 | Beyerlein |
| 7,250,037 B2 | 7/2007 | Shermer et al. |
| 7,267,669 B2 | 9/2007 | Staunton et al. |
| 7,291,132 B2 | 11/2007 | DeRuntz et al. |
| 7,291,159 B2 | 11/2007 | Schmelzeisen-Redeker et al. |
| 7,303,549 B2 | 12/2007 | Flaherty et al. |
| 7,344,385 B2 | 3/2008 | Chen |
| 7,364,570 B2 | 4/2008 | Gerondale et al. |
| 7,390,314 B2 | 6/2008 | Stutz, Jr. et al. |
| 7,407,493 B2 | 8/2008 | Cane' |
| D578,210 S | 10/2008 | Muta et al. |

(56) References Cited

U.S. PATENT DOCUMENTS

| | | |
|---|---|---|
| 7,455,663 B2 | 11/2008 | Bikovsky |
| 7,465,290 B2 | 12/2008 | Reilly |
| 7,488,181 B2 | 2/2009 | van Haaster |
| 7,497,842 B2 | 3/2009 | Diaz et al. |
| 7,501,587 B2 | 3/2009 | English |
| 7,503,786 B2 | 3/2009 | Kato et al. |
| 7,530,964 B2 | 5/2009 | Lavi et al. |
| 7,547,281 B2 | 6/2009 | Hayes et al. |
| 7,565,208 B2 | 7/2009 | Harris et al. |
| 7,569,050 B2 | 8/2009 | Moberg et al. |
| D600,341 S | 9/2009 | Loerwald |
| 7,585,287 B2 | 9/2009 | Bresina et al. |
| 7,588,559 B2 | 9/2009 | Aravena et al. |
| 7,589,974 B2 | 9/2009 | Grady et al. |
| D602,155 S | 10/2009 | Foley et al. |
| D602,586 S | 10/2009 | Foley et al. |
| D604,835 S | 11/2009 | Conley |
| 7,628,770 B2 | 12/2009 | Ethelfeld |
| 7,628,772 B2 | 12/2009 | McConnell et al. |
| 7,628,782 B2 | 12/2009 | Adair et al. |
| 7,637,891 B2 | 12/2009 | Wall |
| 7,637,899 B2 | 12/2009 | Woolston et al. |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,088 B2 | 4/2010 | Sakamoto |
| 7,704,227 B2 | 4/2010 | Moberg et al. |
| 7,704,229 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,776,030 B2 | 8/2010 | Estes et al. |
| 7,780,637 B2 | 8/2010 | Jerde et al. |
| 7,789,857 B2 | 9/2010 | Moberg et al. |
| 7,801,599 B2 | 9/2010 | Young et al. |
| 7,806,868 B2 | 10/2010 | De Polo et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,854,723 B2 | 12/2010 | Hwang et al. |
| 7,857,131 B2 | 12/2010 | Vedrine |
| 7,879,025 B2 | 2/2011 | Jacobson et al. |
| 7,918,825 B2 | 4/2011 | O'Connor et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,967,795 B1 | 6/2011 | Cabiri |
| 7,981,105 B2 | 7/2011 | Adair et al. |
| 7,988,683 B2 | 8/2011 | Adair et al. |
| 7,993,300 B2 | 8/2011 | Nyholm et al. |
| 7,993,301 B2 | 8/2011 | Boyd et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,431 B2 | 11/2011 | Woehr et al. |
| 8,057,436 B2 | 11/2011 | Causey et al. |
| 8,062,253 B2 | 11/2011 | Nielsen et al. |
| 8,066,694 B2 | 11/2011 | Wagener |
| D650,079 S | 12/2011 | Presta et al. |
| D650,903 S | 12/2011 | Kosinski et al. |
| 8,086,306 B2 | 12/2011 | Katzman et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| D657,462 S | 4/2012 | Siroky |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,674 B2 | 4/2012 | Cho et al. |
| 8,162,923 B2 | 4/2012 | Adams et al. |
| 8,167,841 B2 | 5/2012 | Teisen-Simony et al. |
| 8,172,591 B2 | 5/2012 | Wertz |
| 8,172,804 B2 | 5/2012 | Bikovsky |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,221,356 B2 | 7/2012 | Enggaard et al. |
| 8,267,921 B2 | 9/2012 | Yodfat et al. |
| 8,287,520 B2 | 10/2012 | Drew et al. |
| 8,292,647 B1 | 10/2012 | McGrath et al. |
| 8,308,679 B2 | 11/2012 | Hanson et al. |
| 8,323,250 B2 | 12/2012 | Chong et al. |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,465,455 B2 | 6/2013 | Cabiri |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,495,918 B2 | 7/2013 | Bazargan et al. |
| 8,496,862 B2 | 7/2013 | Zelkovich et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,562,364 B2 | 10/2013 | Lin et al. |
| 8,574,216 B2 | 11/2013 | Istoc et al. |
| 8,603,026 B2 | 12/2013 | Favreau |
| 8,603,027 B2 | 12/2013 | Favreau |
| 8,628,510 B2 | 1/2014 | Bazargan et al. |
| 8,674,288 B2 | 3/2014 | Hanson et al. |
| 8,679,060 B2 | 3/2014 | Mernoe et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,801,679 B2 | 8/2014 | Iio et al. |
| 8,810,394 B2 | 8/2014 | Kalpin |
| 8,814,379 B2 | 8/2014 | Griffiths et al. |
| 8,920,374 B2 | 12/2014 | Bokelman et al. |
| 9,061,104 B2 | 6/2015 | Daniel |
| 9,061,110 B2 | 6/2015 | Avery et al. |
| 9,072,827 B2 * | 7/2015 | Cabiri .................. A61M 5/158 |
| 9,089,475 B2 | 7/2015 | Fangrow |
| 9,089,641 B2 | 7/2015 | Kavazov |
| 2001/0025168 A1 | 9/2001 | Gross et al. |

(56) References Cited

U.S. PATENT DOCUMENTS

| | | |
|---|---|---|
| 2001/0041869 A1 | 11/2001 | Causey et al. |
| 2002/0010423 A1 | 1/2002 | Gross et al. |
| 2002/0029018 A1 | 3/2002 | Jeffrey |
| 2002/0040208 A1 | 4/2002 | Flaherty et al. |
| 2002/0055711 A1 | 5/2002 | Lavi et al. |
| 2002/0065488 A1 | 5/2002 | Suzuki et al. |
| 2002/0107487 A1 | 8/2002 | Preuthun |
| 2002/0123740 A1 | 9/2002 | Flaherty et al. |
| 2002/0161332 A1 | 10/2002 | Ramey |
| 2002/0169215 A1 | 11/2002 | Meng |
| 2003/0009133 A1 | 1/2003 | Ramey |
| 2003/0125671 A1 | 7/2003 | Aramata et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0181868 A1 | 9/2003 | Swenson |
| 2004/0010207 A1 | 1/2004 | Flaherty et al. |
| 2004/0092873 A1 | 5/2004 | Moberg |
| 2004/0116866 A1 | 6/2004 | Gorman et al. |
| 2004/0127857 A1 | 7/2004 | Shemesh et al. |
| 2004/0158172 A1 | 8/2004 | Hancock |
| 2004/0186419 A1 | 9/2004 | Cho |
| 2004/0186424 A1 | 9/2004 | Hjertman |
| 2004/0260233 A1 | 12/2004 | Garibotto et al. |
| 2005/0033234 A1 | 2/2005 | Sadowski et al. |
| 2005/0049553 A1 | 3/2005 | Triplett et al. |
| 2005/0065466 A1 | 3/2005 | Vedrine |
| 2005/0065472 A1 | 3/2005 | Cindrich et al. |
| 2005/0071487 A1 | 3/2005 | Lu et al. |
| 2005/0113761 A1 | 5/2005 | Faust et al. |
| 2005/0159706 A1 | 7/2005 | Wilkinson et al. |
| 2005/0171476 A1 | 8/2005 | Judson et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0203461 A1 | 9/2005 | Flaherty et al. |
| 2005/0238507 A1 | 10/2005 | DiIanni et al. |
| 2005/0283114 A1 | 12/2005 | Bresina et al. |
| 2006/0013716 A1 | 1/2006 | Nason et al. |
| 2006/0030816 A1 | 2/2006 | Zubry |
| 2006/0095014 A1 | 5/2006 | Ethelfeld |
| 2006/0122577 A1 | 6/2006 | Poulsen et al. |
| 2006/0173406 A1 | 8/2006 | Hayes et al. |
| 2006/0173410 A1 | 8/2006 | Moberg et al. |
| 2006/0173439 A1 | 8/2006 | Thorne et al. |
| 2006/0195029 A1 | 8/2006 | Shults et al. |
| 2006/0211982 A1 | 9/2006 | Prestrelski et al. |
| 2006/0229569 A1 | 10/2006 | Lavi et al. |
| 2006/0264889 A1 | 11/2006 | Moberg et al. |
| 2006/0264890 A1 | 11/2006 | Moberg et al. |
| 2006/0264894 A1 | 11/2006 | Moberg et al. |
| 2006/0270987 A1 | 11/2006 | Peter |
| 2006/0283465 A1 | 12/2006 | Nickel et al. |
| 2006/0293722 A1 | 12/2006 | Slatkine et al. |
| 2007/0021733 A1 | 1/2007 | Hansen et al. |
| 2007/0049865 A1 | 3/2007 | Radmer et al. |
| 2007/0073228 A1 | 3/2007 | Mernoe et al. |
| 2007/0106218 A1 | 5/2007 | Yodfat et al. |
| 2007/0118405 A1 | 5/2007 | Campbell et al. |
| 2007/0129688 A1 | 6/2007 | Scheurer et al. |
| 2007/0167912 A1 | 7/2007 | Causey et al. |
| 2007/0185449 A1 | 8/2007 | Mernoe |
| 2007/0197968 A1 | 8/2007 | Pongpairochana et al. |
| 2007/0203454 A1 | 8/2007 | Shermer et al. |
| 2007/0233038 A1 | 10/2007 | Pruitt et al. |
| 2007/0282269 A1 | 12/2007 | Carter et al. |
| 2008/0021439 A1 | 1/2008 | Brittingham et al. |
| 2008/0033367 A1 | 2/2008 | Haury et al. |
| 2008/0033369 A1 | 2/2008 | Kohlbrenner et al. |
| 2008/0033393 A1 | 2/2008 | Edwards et al. |
| 2008/0051711 A1 | 2/2008 | Mounce et al. |
| 2008/0051730 A1 | 2/2008 | Bikovsky |
| 2008/0059133 A1 | 3/2008 | Edwards et al. |
| 2008/0097381 A1 | 4/2008 | Moberg et al. |
| 2008/0108951 A1 | 5/2008 | Jerde et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0167641 A1 | 7/2008 | Hansen et al. |
| 2008/0188813 A1 | 8/2008 | Miller et al. |
| 2008/0195049 A1 | 8/2008 | Thalmann et al. |
| 2008/0208138 A1 | 8/2008 | Lim et al. |
| 2008/0215006 A1 | 9/2008 | Thorkild |
| 2008/0215015 A1 | 9/2008 | Cindrich et al. |
| 2008/0243087 A1 | 10/2008 | Enggaard et al. |
| 2008/0249473 A1 | 10/2008 | Rutti et al. |
| 2008/0262436 A1 | 10/2008 | Olson |
| 2008/0269687 A1 | 10/2008 | Chong et al. |
| 2008/0269723 A1 | 10/2008 | Mastrototaro et al. |
| 2008/0274630 A1 | 11/2008 | Shelton et al. |
| 2008/0275407 A1 | 11/2008 | Scheurer |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0041805 A1 | 2/2009 | Walker |
| 2009/0043253 A1 | 2/2009 | Podaima |
| 2009/0048347 A1 | 2/2009 | Cohen et al. |
| 2009/0054750 A1 | 2/2009 | Jennewine |
| 2009/0062767 A1 | 3/2009 | Van Antwerp et al. |
| 2009/0069784 A1 | 3/2009 | Estes et al. |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1 | 4/2009 | Gross et al. |
| 2009/0105650 A1 | 4/2009 | Wiegel et al. |
| 2009/0124977 A1 | 5/2009 | Jensen |
| 2009/0139724 A1 | 6/2009 | Gray et al. |
| 2009/0143730 A1 | 6/2009 | De Polo et al. |
| 2009/0143735 A1 | 6/2009 | De Polo et al. |
| 2009/0149830 A1 | 6/2009 | Spector |
| 2009/0182277 A1 | 7/2009 | Carter |
| 2009/0204076 A1 | 8/2009 | Liversidge |
| 2009/0209896 A1 | 8/2009 | Selevan |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0281585 A1 | 11/2009 | Katzman et al. |
| 2009/0299290 A1 | 12/2009 | Moberg |
| 2009/0299397 A1 | 12/2009 | Ruan et al. |
| 2009/0326459 A1 | 12/2009 | Shipway et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0049128 A1 | 2/2010 | McKenzie et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0137831 A1 | 6/2010 | Tsals |
| 2010/0145303 A1 | 6/2010 | Yodfat et al. |
| 2010/0145305 A1 | 6/2010 | Alon |
| 2010/0162548 A1 | 7/2010 | Leidig |
| 2010/0168607 A1 | 7/2010 | Miesel |
| 2010/0168683 A1 | 7/2010 | Cabiri |
| 2010/0198157 A1 | 8/2010 | Gyrn et al. |
| 2010/0204657 A1 | 8/2010 | Yodfat et al. |
| 2010/0234767 A1 | 9/2010 | Sarstedt |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0274202 A1 | 10/2010 | Hyde et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |

(56) References Cited

U.S. PATENT DOCUMENTS

| | | |
|---|---|---|
| 2011/0054399 A1 | 3/2011 | Chong et al. |
| 2011/0054400 A1 | 3/2011 | Chong et al. |
| 2011/0066131 A1 | 3/2011 | Cabiri |
| 2011/0125056 A1 | 5/2011 | Merchant |
| 2011/0160654 A1 | 6/2011 | Hanson et al. |
| 2011/0160655 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0172745 A1 | 7/2011 | Na et al. |
| 2011/0178463 A1 | 7/2011 | Cabiri |
| 2011/0178472 A1 | 7/2011 | Cabiri |
| 2011/0201998 A1 | 8/2011 | Pongpairochana et al. |
| 2011/0238031 A1 | 9/2011 | Adair et al. |
| 2011/0245773 A1 | 10/2011 | Estes et al. |
| 2011/0270160 A1 | 11/2011 | Mernoe |
| 2011/0282282 A1 | 11/2011 | Lorenzen et al. |
| 2011/0282296 A1 | 11/2011 | Harms et al. |
| 2011/0295205 A1 | 12/2011 | Kaufmann et al. |
| 2011/0313238 A1 | 12/2011 | Reichenbach et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022344 A1 | 1/2012 | Kube |
| 2012/0022499 A1 | 1/2012 | Anderson et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041414 A1 | 2/2012 | Estes et al. |
| 2012/0059332 A1 | 3/2012 | Woehr et al. |
| 2012/0071819 A1 | 3/2012 | Bruggemann et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0129362 A1 | 5/2012 | Hampo et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0226234 A1 | 9/2012 | Bazargan et al. |
| 2012/0259282 A1 | 10/2012 | Alderete, Jr. et al. |
| 2013/0012875 A1 | 1/2013 | Gross et al. |
| 2013/0068319 A1 | 3/2013 | Plumptre et al. |
| 2013/0085457 A1 | 4/2013 | Schiff et al. |
| 2013/0089992 A1 | 4/2013 | Yang |
| 2013/0096509 A1 | 4/2013 | Avery et al. |
| 2013/0110049 A1 | 5/2013 | Cronenberg et al. |
| 2013/0133438 A1 | 5/2013 | Kow et al. |
| 2013/0237953 A1 | 9/2013 | Kow et al. |
| 2013/0245595 A1 | 9/2013 | Kow et al. |
| 2013/0245596 A1 | 9/2013 | Cabiri et al. |
| 2013/0253419 A1 | 9/2013 | Favreau |
| 2013/0253420 A1 | 9/2013 | Favreau |
| 2013/0253421 A1 | 9/2013 | Favreau |
| 2013/0296799 A1 | 11/2013 | Degtiar et al. |
| 2013/0304021 A1 | 11/2013 | Cabiri et al. |
| 2013/0323699 A1 | 12/2013 | Edwards et al. |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1 | 5/2014 | Anderson et al. |
| 2014/0148785 A1 | 5/2014 | Moberg et al. |
| 2014/0163522 A1 | 6/2014 | Alderete, Jr. et al. |
| 2014/0194819 A1 | 7/2014 | Maule et al. |
| 2014/0194854 A1 | 7/2014 | Tsals |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0213975 A1 | 7/2014 | Clemente et al. |
| 2014/0236087 A1 | 8/2014 | Alderete, Jr. et al. |
| 2014/0261758 A1 | 9/2014 | Wlodarczyk et al. |

FOREIGN PATENT DOCUMENTS

| | | |
|---|---|---|
| CN | 101090749 A | 12/2007 |
| CN | 201941304 U | 8/2011 |
| CN | 102186733 A | 9/2011 |
| DE | 1064693 B | 9/1959 |
| EP | 0017412 A1 | 10/1980 |
| EP | 0222656 A1 | 5/1987 |
| EP | 0401179 A1 | 12/1990 |
| EP | 1530979 A1 | 5/2005 |
| EP | 1666080 A1 | 6/2006 |
| EP | 2060606 A1 | 5/2009 |
| EP | 2498589 A1 | 9/2012 |
| JP | H07-194701 A | 8/1995 |
| JP | H09-505758 A | 6/1997 |
| JP | 2001-512992 A | 8/2001 |
| JP | 2002-505601 A | 2/2002 |
| JP | 2002-507459 A | 3/2002 |
| JP | 2002-528676 A | 9/2002 |
| JP | 2003-501157 A | 1/2003 |
| JP | 2003-527138 A | 9/2003 |
| JP | 2003-534061 A | 11/2003 |
| JP | 2004-501721 A | 1/2004 |
| JP | 2004-512100 A | 4/2004 |
| JP | 2005-523127 A | 8/2005 |
| JP | 2005-270629 A | 10/2005 |
| JP | 2007-509661 A | 4/2007 |
| JP | 2008-534131 A | 8/2008 |
| JP | 2008-220961 A | 9/2008 |
| JP | 2009-502273 A | 1/2009 |
| WO | 9009202 A1 | 8/1990 |
| WO | 9307922 A1 | 4/1993 |
| WO | 9407553 A1 | 4/1994 |
| WO | 9513838 A1 | 5/1995 |
| WO | 9609083 A1 | 3/1996 |
| WO | 9632975 A1 | 10/1996 |
| WO | 9700091 A1 | 1/1997 |
| WO | 9710012 A1 | 3/1997 |
| WO | 9733638 A1 | 9/1997 |
| WO | 9857683 A1 | 12/1998 |
| WO | 9929151 A1 | 6/1999 |
| WO | 9959665 A1 | 11/1999 |
| WO | 0025844 A1 | 5/2000 |
| WO | 0187384 A1 | 11/2001 |
| WO | 0189607 A2 | 11/2001 |
| WO | 0189613 A1 | 11/2001 |
| WO | 0234315 A1 | 5/2002 |
| WO | 02072182 A1 | 9/2002 |
| WO | 02002165 A2 | 10/2002 |
| WO | 03090833 A1 | 11/2003 |
| WO | 2004032990 A2 | 4/2004 |
| WO | 2004105841 A1 | 12/2004 |
| WO | 2005018703 A2 | 3/2005 |
| WO | 2005037350 A2 | 4/2005 |
| WO | 2006037434 A1 | 4/2006 |
| WO | 2006069380 A1 | 6/2006 |
| WO | 2006102676 A1 | 9/2006 |
| WO | 2006104806 A2 | 10/2006 |
| WO | 2007051563 A1 | 5/2007 |
| WO | 2007056504 A1 | 5/2007 |
| WO | 2008001377 A2 | 1/2008 |
| WO | 2008014908 A1 | 2/2008 |
| WO | 2008057976 A2 | 5/2008 |
| WO | 2008072229 A2 | 6/2008 |
| WO | 2008076459 A1 | 6/2008 |
| WO | 2008078318 A2 | 7/2008 |
| WO | 2009044401 | 4/2009 |
| WO | 2009046989 A2 | 4/2009 |
| WO | 2009125398 A2 | 10/2009 |
| WO | 2009144085 A2 | 12/2009 |
| WO | 2010078227 A1 | 7/2010 |
| WO | 2010078242 A1 | 7/2010 |

(56) References Cited

FOREIGN PATENT DOCUMENTS

| WO | 2011075105 | A1 | 6/2011 |
|---|---|---|---|
| WO | 2011090955 | A1 | 7/2011 |
| WO | 2011090956 | A2 | 7/2011 |
| WO | 2011156373 | A1 | 12/2011 |
| WO | 2012032411 | A2 | 3/2012 |
| WO | 2012040528 | A1 | 3/2012 |
| WO | 2012160157 | A1 | 11/2012 |
| WO | 2014179774 | A1 | 11/2014 |

OTHER PUBLICATIONS

Office Action issued May 7, 2015 in JP Application No. 2012-550069.
Office Action issued May 13, 2015 in CN Application No. 201380025566.3.
U.S. Appl. No. 14/725,009 by Bar-El, filed May 29, 2015.
Office Action issued May 1, 2015 in U.S. Appl. No. 14/638,525 by Filman.
Office Action issued Jun. 4, 2015 in U.S. Appl. No. 13/667,739 by Cabiri.
Office Action issued Nov. 4, 2013 in EP Application No. 11 709 234.6.
Office Action issued Dec. 17, 2013 in JP Application No. 2012-529808.
Office Action issued Dec. 10, 2013 in CN Application No. 201180006567.4.
Office Action issued Jan. 8, 2014 in U.S. Appl. No. 13/521,167 by Cabiri.
U.S. Appl. No. 29/479,307 by Norton, filed Jan. 14, 2014.
U.S. Appl. No. 14/193,692 by Gross, filed Feb. 28, 2014.
Office Action issued Feb. 4, 2014 in EP Application No. 11 707 942.6.
English translation of an Office Action issued Mar. 5, 2014 in CN Application No. 200880117084.X.
Int'l Search Report and Written Opinion issued Apr. 3, 2014 in Int'l Application No. PCT/US2013/078040.
Extended European Search Report issued Mar. 27, 2014 in EP Application No. 14154717.4.
Office Action issued Feb. 28, 2014 in CN Application No. 201180006571.0.
U.S. Appl. No. 14/258,661 by Cabiri, filed Apr. 22, 2014.
Int'l Search Report and Written Opinion issued Jan. 7, 2014 in Int'l Application No. PCT/US2013/065211.
Office Action issued May 23, 2014 in U.S. Appl. No. 13/472,112 by Cabiri.
Office Action issued Jun. 3, 2014 in JP Application No. 2010-527595.
Office Action issued Jul. 7, 2014 in U.S. Appl. No. 12/244,666 by Gross.
Int'l Search Report and Written Opinion issued Jul. 31, 2014 in Int'l Application No. PCT/US2014/033598.
Extended European Search Report issued Aug. 7, 2014 in EP Application No. 1417477.4.
Office Action issued Aug. 6, 2014 in EP Application No. 11 707 942.6.
Office Action issued Sep. 2, 2014 in JP Application No. 2012-550069.
Office Action issued Sep. 2, 2014 in JP Application No. 2012-550068.
Office Action issued Aug. 26, 2014 in CN Application No. 201180006567.4.
Int'l Preliminary Report on Patentability issued Oct. 9, 2014 in Int'l Application No. PCT/US2013/033118.
Office Action issued Oct. 9, 2014 in U.S. Appl. No. 13/873,335.
Office Action issued Nov. 5, 2014 in U.S. Appl. No. 13/643,470 by Alon.
U.S. Appl. No. 14/553,399 by Cabiri, filed Nov. 25, 2014.
Office Action issued Nov. 2, 2014 in CN Application No. 201180006571.0.
Office Action issued Nov. 21, 2014 in U.S. Appl. No. 13/472,112 by Cabiri.
Office Action issued Nov. 21, 2014 in U.S. Appl. No. 13/429,840 by Cabiri.
Int'l Preliminary Report on Patentability issued Nov. 27, 2014 in Int'l Application No. PCT/US2013/039465.
U.S. Appl. No. 14/593,051 by Gross, filed Jan. 9, 2015.
U.S. Appl. No. 14/683,193 by Cabiri, filed Apr. 10, 2015.
Office Action issued Feb. 20, 2015 in U.S. Appl. No. 13/521,181 by Cabiri.
Office Action issued Feb. 24, 2015 in U.S. Appl. No. 14/258,661 by Cabiri.
U.S. Appl. No. 14/638,525 by Filman, filed Mar. 4, 2015.
Extended European Search Report issued Feb. 23, 2015 in EP Application No. 14166596.8.
Office Action issued Mar. 10, 2015 in U.S. Appl. No. 13/643,470 by Alon.
Office Action issued Mar. 10, 2015 in U.S. Appl. No. 12/244,666 by Gross.
Extended European Search Report issued Feb. 23, 2015 in EP Application No. 14166591.9.
Office Action issued Mar. 10, 2015 in CN Application No. 201180006567.4.
Office Action issued Mar. 31, 2015 in JP Application No. 2012-550068.
U.S. Appl. No. 13/429,840 by Cabiri, filed Mar. 26, 2012.
Daikyo Crystal Zenith® polymer, Manufactured by Daikyo Seiko, Ltd. (Jun. 25, 2008).
Copaxone®, Manufactured by Teva Pharmaceutical Industries Ltd. (2009).
Int'l Search Report issued May 13, 2009 in Int'l Application No. PCT/IL2008/001312.
Int'l Preliminary Report on Patentability issued Apr. 7, 2010 in Int'l Application No. PCT/IL2008/001312; Written Opinion.
Int'l Search Report issued Apr. 26, 2010 in Int'l Application No. PCT/US2009/069552.
Office Action issued Apr. 5, 2010 in U.S. Appl. No. 12/244,666.
Office Action issued Sep. 21, 2010 in U.S. Appl. No. 12/244,666.
Office Action issued Apr. 5, 2010 in U.S. Appl. No. 12/244,688.
Office Action issued Sep. 2, 2010 in U.S. Appl. No. 12/244,688.
Office Action issued Sep. 30, 2010 in U.S. Appl. No. 12/689,250.
Int'l Search Report issued Jan. 12, 2011 in Int'l Application No. PCT/US2010/048556; Written Opinion.
U.S. Appl. No. 60/997,459, filed Oct. 2, 2007.
U.S. Appl. No. 12/559,563, filed Sep. 15, 2009.
U.S. Appl. No. 12/689,249, filed Jan. 19, 2010.
U.S. Appl. No. 12/689,250, filed Jan. 19, 2010.
International Preliminary Report on Patentability issued on Jul. 5, 2011 in International Application No. PCT/US2009/069552; Written Opinion.
Office Action issued Jul. 13, 2011 in U.S. Appl. No. 12/559,563.
Int'l Preliminary Report on Patentability issued Sep. 1, 2011 in Int'l Application No. PCT/US2010/048556.
Office Action issued Sep. 6, 2011 in U.S. Appl. No. 12/345,818.
Office Action issued Feb. 21, 2012 in U.S. Appl. No. 12/689,249.
Int'l Search Report issued Jun. 17, 2011 in Int'l Application No. PCT/US2011/021604.
Int'l Search Report issued Oct. 12, 2011 in Int'l Application No. PCT/US2011/021605.
Office Action issued Oct. 28, 2011 in U.S. Appl. No. 12/615,828.
Int'l Search Report issued Sep. 22, 2011 in Int'l Application No. PCT/IL11/00368; Written Opinion.
U.S. Appl. No. 13/521,181 by Cabiri, filed Jul. 9, 2012.
U.S. Appl. No. 13/521,167 by Cabiri, filed Jul. 9, 2012.
Office Action issued May 16, 2012 in U.S. Appl. No. 12/615,828.
Office Action issued Jul. 2, 2012 in U.S. Appl. No. 13/272,555.
Office Action issued May 3, 2012 in CN Application No. 200880117084.X.
U.S. Appl. No. 13/472,112 by Cabiri, filed May 15, 2012.
Int'l Preliminary Report on Patentability issued Aug. 2, 2012 in Int'l Application No. PCT/US2011/021604.
U.S. Appl. No. 13/643,470 by Alon, filed Oct. 25, 2012.
U.S. Appl. No. 13/733,516 by Cabiri, filed Jan. 3, 2013.
Office Action issued Jan. 8, 2013 in JP Application No. 2010-527595.

(56) References Cited

OTHER PUBLICATIONS

Int'l Preliminary Report on Patentability issued Feb. 7, 2013 in Int'l Application No. PCT/US2011/021604.
Int'l Preliminary Report on Patentability issued Feb. 7, 2013 in Int'l Application No. PCT/US2011/021605.
English translation of an Office Action issued Jan. 30, 2013 in CN Application No. 200880117084.X.
U.S. Appl. No. 13/873,335 by Filman, filed Apr. 30, 2013.
U.S. Appl. No. 13/892,905 by Cabiri, filed May 13, 2013.
U.S. Appl. No. 13/874,121 by Degtiar, filed Apr. 30, 2013.
U.S. Appl. No. 13/874,085 by Cabiri, filed Apr. 30, 2013.
U.S. Appl. No. 13/874,017 by Cabiri, filed Apr. 30, 2013.
Int'l Search Report and Written Opinion issued Jul. 26, 2013 in Int'l Application No. PCT/US2012/039465.
Int'l Search Report and Written Opinion issued Aug. 5, 2013 in Int'l Application No. PCT/US2013/033118.
U.S. Appl. No. 13/964,651 by Gross, filed Aug. 12, 2013.
Office Action issued Aug. 15, 2013 in CN Application No. 200880117084.X.
Office Action issued Oct. 9, 2013 in IL Application No. 208634.
Office Action issued Nov. 5, 2013 in JP Application No. 2010-527595.
Office Action issued Sep. 29, 2013 in CN Application No. 201080040968.7.
Office Action issued Jul. 31, 2015 in U.S. Appl. No. 13/521,181 by Cabiri.
Office Action issued Aug. 13, 2015 in U.S. Appl. No. 14/553,399 by Cabiri.
Int'l Preliminary Report on Patentability issued Jul. 16, 2015 in Int'l Application No. PCT/US2013/078040.
Notice of Allowance issued Aug. 24, 2015 in U.S. Appl. No. 29/479,307 by Norton.
Office Action issued Sep. 9, 2015 in U.S. Appl. No. 13/643,470 by Alon.
U.S. Appl. No. 14/850,450 by Gross, filed Sep. 10, 2015.
U.S. Appl. No. 14/861,478 by Cabiri, filed Sep. 22, 2015.
U.S. Appl. No. 14/880,673 by Cabiri, filed Oct. 12, 2015.
Office Action issued Sep. 30, 2015 in U.S. Appl. No. 13/667,739 by Cabiri.
Office Action issued Sep. 18, 2015 in U.S. Appl. No. 13/874,085 by Cabiri.
Office Action issued Dec. 17, 2015 in CN Application No. 201380017192.0.
U.S. Appl. No. 14/931,439 by Cabiri, filed Nov. 3, 2015.
Office Action issued Feb. 19, 2016 in U.S. Appl. No. 14/553,399 by Cabiri.
Notice of Allowance issued Apr. 25, 2016 in U.S. Appl. No. 14/553,399 by Cabiri.
Office Action issued Feb. 3, 2016 in U.S. Appl. No. 14/931,439 by Cabiri.
Office Action issued May 4, 2016 in U.S. Appl. No. 15/069,080 by Cabiri.
Notice of Allowance issued May 11, 2016 in U.S. Appl. No. 14/931,439 by Cabiri.

* cited by examiner

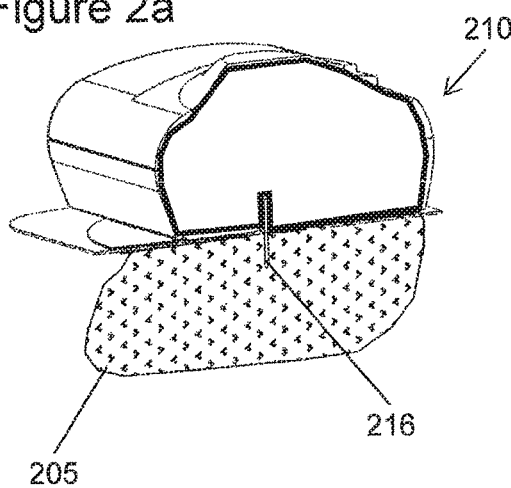

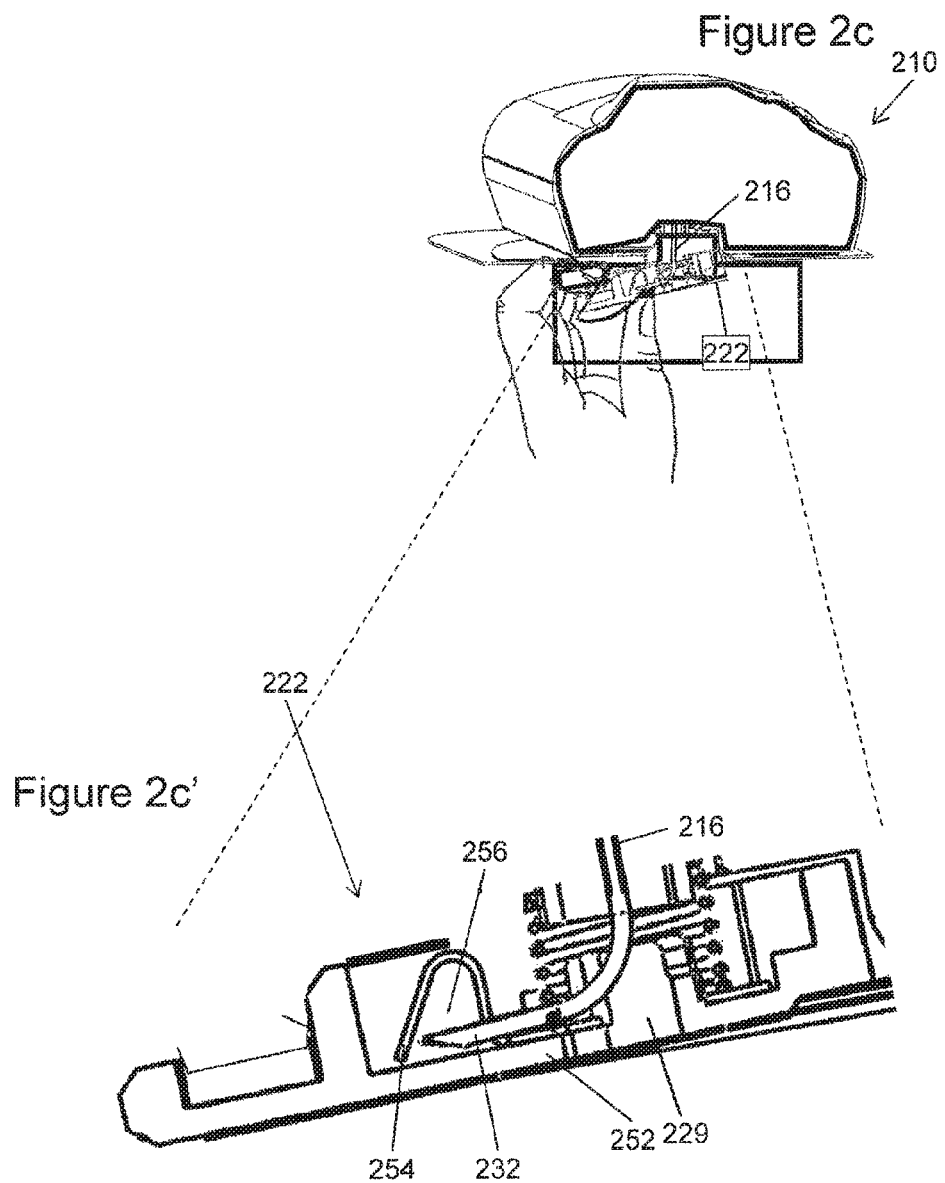

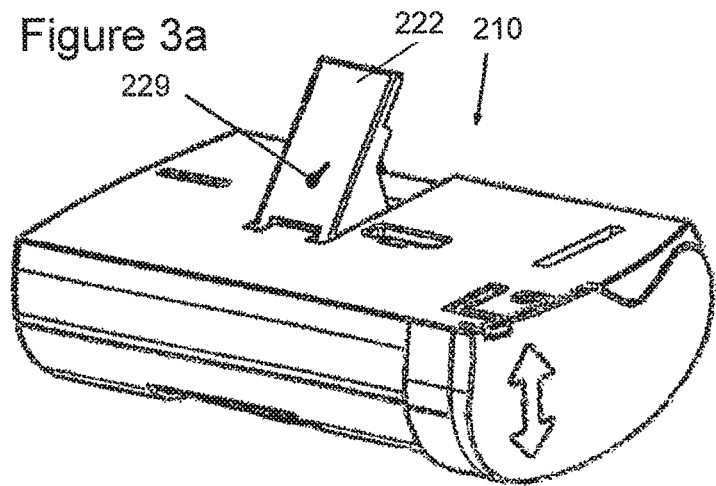
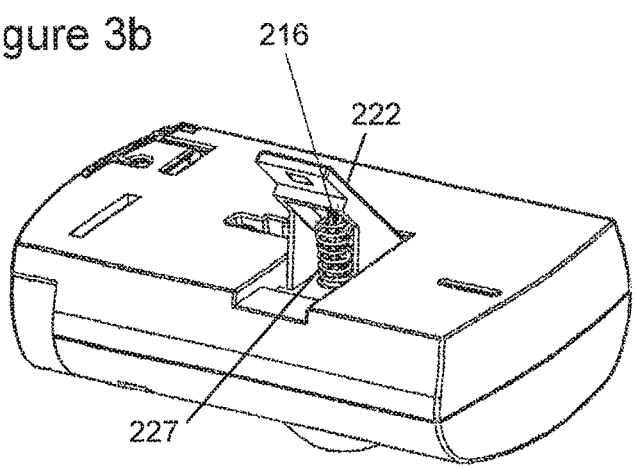

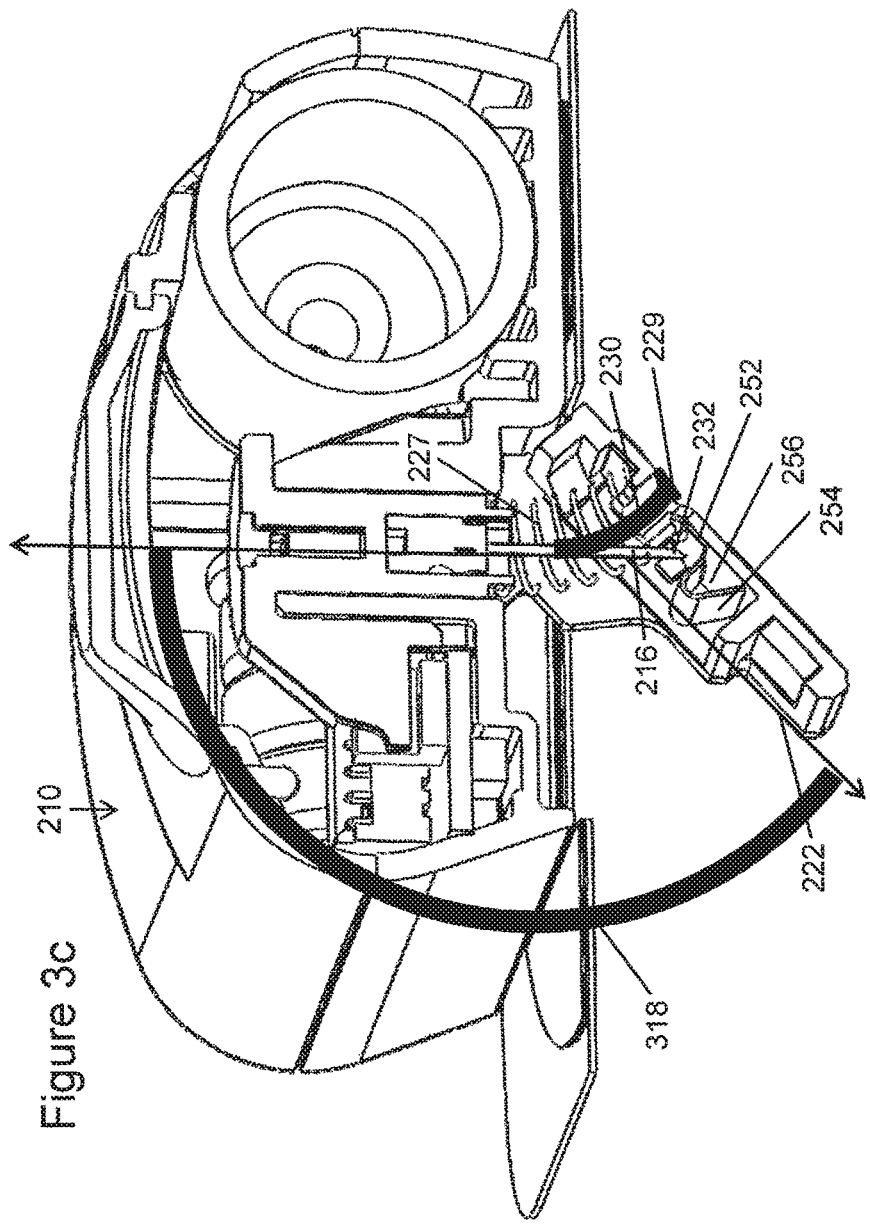

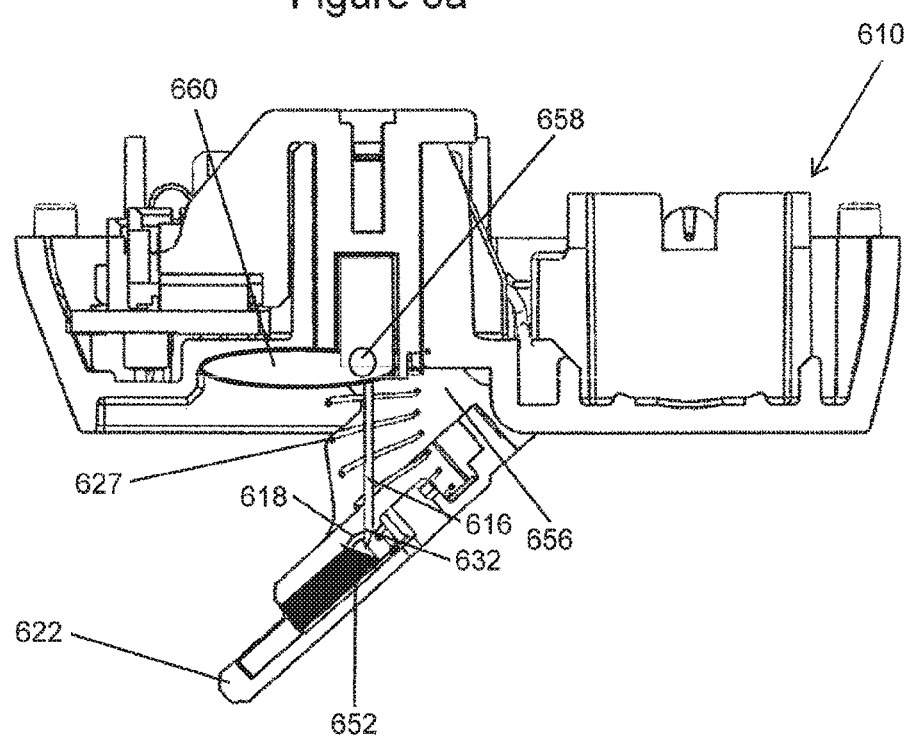

FAIL SAFE POINT PROTECTOR FOR NEEDLE SAFETY FLAP

CROSS REFERENCE TO RELATED APPLICATIONS

This application is a continuation of U.S. application Ser. No. 13/429,840, filed Mar. 26, 2012, entitled "Fail Safe Point Protector For Needle Safety Flap," now U.S. Pat. No. 9,072,827, issued Jul. 7, 2015, the disclosure of which is incorporated herein by reference in its entirety.

BACKGROUND OF THE INVENTION

The present invention, in some embodiments thereof, relates to a system and method for preventing a reexposure of point of a needle by deflecting the point and more particularly, but not exclusively, to a guide and/or a safety clip for deflecting and/or enclosing the point upon collapse of a needle protector flap.

International Patent Application WO 2011090955 to Oz Cabiri discloses a needle assembly adapted for fluid communication with a cartridge containing a substance to be delivered to a subject, the needle assembly is characterized by a biasing device arranged to apply a biasing force on a needle to cause the needle to protrude outwards of a housing to pierce the subject. A safety latch is movably mounted on the housing and formed with a needle opening to allow the needle to pass therethrough. The safety latch has a first position wherein the needle is aligned to pass through the needle opening and a second position wherein the safety latch is moved with respect to the housing and the needle is blocked by a portion of the safety latch distanced from the needle opening.

U.S. Pat. No. 5,300,045 and International Application WO 2008/014908 to Plassche discloses a stylet which is received in a needle cannula and is automatically capped in a guard body when the stylet is withdrawn from the cannula. The guard contains an arm which moves into blocking position with respect to the tip of the stylet when it is withdrawn from the cannula by following a cam surface on the cannula hub (either inside or outside the hub for different styles of needle cannulas). The arm may be spring biased, across a hole in the guard in which the stylet is slidably disposed into interfering relationship with the arm. The cam surface urges the arm to bring a portion thereof which protects the point of the tip of the stylet and captures it inside the guard. The arm and cam prevent removal of the stylet from the cannula until the tip is covered and protected by the guard, thereby automatically capping the tip of the stylet to prevent potentially dangerous, inadvertent, or accidental sticking of medical personnel.

U.S. Pat. No. 5,836,920 to Robertson discloses a guard for a hypodermic needle that includes a hub for attachment to a needle and a shield which can be attached to the hub. The shield is adapted to lie adjacent the needle and has a lip which projects outwardly to cover the tip of the needle. An enclosure for the tip of the needle is provided and located adjacent to the lip. The hub and the shield each includes complementary attachment mechanisms whereby the shield can be attached to the hub in first and second relative positions. In the first position, the needle can be used and the shield is capable of moving away from the needle to uncover the tip as the needle initially penetrates the body of a patient and of returning back toward the needle and again to cover the tip as the needle is withdrawn from the patient. By pulling the shield toward the hub in a direction substantially parallel to the longitudinal axis of the needle, the shield is attached to the hub in a second relative position wherein the tip of the needle is enclosed by the enclosure and thereby locks the shield in position with respect to the needle so that the shield cannot be flexed away from the needle to uncover the tip after use.

U.S. Published Patent Application, 2011/0282296 to Harms discloses a protective cap coupled to a syringe having a needle attached thereto. The protective cap may be pivoted to a position in alignment with the needle so that the protective cap substantially envelops the needle. A plug may be inserted into the cap to envelop or capture the needle within a hollow body of the plug to secure at least a tip of the needle.

Additional background art includes U.S. Published Patent Application 2010/0168683 to Oz Cabiri, U.S. Published Patent Application 2010/0234767 Sarstedt, U.S. Published Patent Application 2008/0208138 to Kiang, U.S. Published Patent Application 2003/0135159 to Daily, U.S. Published Patent Application 2002/0055711 to Lavi, U.S. Pat. No. 8,057,431 to Woehr, U.S. Pat. No. 7,854,723 to Hwang, U.S. Pat. No. 6,224,569 to Brimhall, and U.S. Pat. No. 4,929,241 to Kulli.

BRIEF SUMMARY OF THE INVENTION

According to an aspect of some embodiments of the present invention there is provided a device for preventing reexposure of a point of a needle projecting from a housing of an apparatus wearable by a recipient for delivering a drug to the recipient. The device may include a flap movably mounted to a housing of the apparatus. The flap may have a protecting position in which the flap may cover the point. The device may further include a secure space. The device may further include a guide integrated into the flap. The guide may be positioned relative to the point such that upon collapse of the flap the guide deflects the point into the secure space thereby preventing the reexposure of the point upon the collapse.

According to some embodiments of the invention, in the protecting position, the guide may be disposed at an incline to the needle. The incline may be at an angle of between 5 and 85 degrees to the needle According to some embodiments of the invention, the device may further include a clip shielding the secure space.

According to some embodiments of the invention, after the collapse of the flap, the secure space may be shielded by a clip and/or the flap and/or a joint between the flap and the housing.

According to some embodiments of the invention, the device may further include a pivot linking the needle and the housing. The pivot may be positioned to rotate upon deflection of the needle.

According to some embodiments of the invention, the device may further include a translating support linking the needle and the housing. The translating support may be positioned to translate upon deflection of the needle.

According to some embodiments of the invention, the guide may be positioned to bend the needle when the needle is deflected.

According to some embodiments of the invention, the guide may include a channel positioned to direct the point of the needle toward the secure space.

According to some embodiments of the invention, the guide may include a barrier positioned to direct the point to the secure space.

According to some embodiments of the invention, the flap may be pivotally connected to the housing of the apparatus.

According to some embodiments of the invention, the flap may have an exposing position wherein the needle protrudes through an opening in the flap. The opening may be non-circular.

According to some embodiments of the invention, the device may further include a biasing device for moving the flap from the exposing position to the protecting position.

According to some embodiments of the invention, in the protecting position, the opening may be not aligned with the point.

According to an aspect of some embodiments of the present invention there is provided a device for preventing reexposure of a point of a needle projecting from a housing of an apparatus. The apparatus may be wearable by a recipient. The apparatus may deliver a drug to the recipient. The device may include a flap movably mounted to the housing of the apparatus. The flap may have at least three positions: an exposed position in which the needle protrudes through an opening in the flap; and a protecting position in which the flap covers the point and the point is not aligned with the opening; and a collapsed position. The device may also include a secure location in the collapsed position. The device may also include a guide integrated into the flap. The guide may be positioned relative to the point of the needle such that upon movement of the flap from the protecting position to the collapsed position the guide deflects the point into the secure space thereby preventing the reexposure of the point upon collapsing of the protective flap.

According to some embodiments of the invention, in the protecting position, the guide may be disposed at an incline to the needle.

According to some embodiments of the invention, the incline between the guide and the needle in the protected position may be at an angle of between 5 and 85 degrees.

According to some embodiments of the invention, the device may further include a clip shielding the secure space.

According to some embodiments of the invention, after the collapse of the flap, the secure space may be shielded by a clip and/or the flap and/or a joint between the flap and the housing of the apparatus.

According to some embodiments of the invention, the device may further include a pivot linking the needle and the housing. The pivot may be positioned to rotate when the needle is deflected.

According to some embodiments of the invention, the device may further include a translating support linking the needle and the housing. The translating support may be positioned to translate upon deflection of the needle.

According to some embodiments of the invention, the guide may be positioned to bend the needle upon the deflection of the needle.

According to some embodiments of the invention, the guide may include a channel positioned to direct the point of the needle toward the secure space.

According to some embodiments of the invention, the guide may include a barrier positioned to direct the point of the needle toward the secure space.

According to some embodiments of the invention, the flap may be pivotally connected to the housing.

According to some embodiments of the invention, the device may further include a biasing device for moving the flap from the exposing position to the protecting position.

According to some embodiments of the invention, the needle opening in the flap may be non-circular.

According to an aspect of some embodiments of the present invention there is provided a method of preventing reexposure of a point of a needle projecting from a housing of a portable injection apparatus upon collapse of a protective flap. The method may include covering the point after use of the apparatus by moving the protective flap to a protecting position, and deflecting the point into a secure space upon a collapse of the protective flap to prevent the reexposure of the point.

According to some embodiments of the invention, the method may further include shielding the secure space.

According to some embodiments of the invention, the method may further include pivoting the needle around a needle support when the needle is deflected. The needle support may link the needle and the housing.

According to some embodiments of the invention, the method may further include translating a needle support that links the needle and the housing upon the deflection of the needle.

According to some embodiments of the invention, the method may further include bending the needle upon the deflection of the needle.

According to some embodiments of the invention, the method may further include pivoting the protective flap from an exposing position wherein the needle protrudes through an opening in the protective flap to the protecting position.

According to an aspect of some embodiments of the present invention there is provided a device for preventing a needle stick by a point of a needle projecting from a housing of an apparatus wearable by a recipient for delivering a drug to the recipient. The device may include a flap movably mounted to a housing of the apparatus. The device may also include a non-circular opening in the flap. The needle may project through the non-circular opening when the flap is in an exposing position. The device may further include a biasing mechanism for moving the flap to a protecting position in which the flap covers the point and the non-circular opening is not aligned with the point.

According to an aspect of some embodiments of the present invention there is provided a device for preventing a needle stick by a point of a needle projecting from a housing of an apparatus wearable by a recipient for delivering a drug to the recipient. The device may include a flap movably mounted to a housing of the apparatus and an opening in the flap. The needle may project through the opening when the flap is in an exposing position. The device may also include a biasing mechanism for moving the flap to a protecting position in which the flap covers the point of the needle. In the protecting position, the opening may not be aligned with the point. The device may also include a translating needle support linking the needle and the housing.

According to an aspect of some embodiments of the present invention there is provided a device for preventing a needle stick by a point of a needle projecting from a housing of an apparatus wearable by a recipient for delivering a drug to the recipient. The device may include a flap movably mounted to a housing of the apparatus and an opening in the flap. The needle may project through the opening when the flap is in an exposing position. The device may also include a biasing mechanism for moving the flap to a protecting position in which the flap covers the point of the needle. In the protecting position, the opening may not be aligned with the point. The device may also include a pivoting needle support linking the needle and the housing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 2a' is a perspective illustration of an exemplary embodiment drug pump with a flap in an exposing position;

FIGS. 2c and 2c' are a close up cutaway view of the flap after collapse;

FIG. 3a is a perspective view of the embodiment of FIG. 2 with the flap in a protecting position;

FIG. 3b is a view of the embodiment of FIG. 2 with the flap in a protecting position, from another perspective;

FIG. 3c is a cutaway illustration of the embodiment of FIG. 2 with the flap in the protecting position;

FIG. 3d' is a close up base view of oval A of FIG. 3d showing the form of the needle opening.

FIG. 4' is an expanded view of circle B of FIG. 4;

FIG. 6a is a cutaway view of a further additional embodiment of an injector with a flap in a protecting position;

DETAILED DESCRIPTION OF THE INVENTION

Figure 1A:
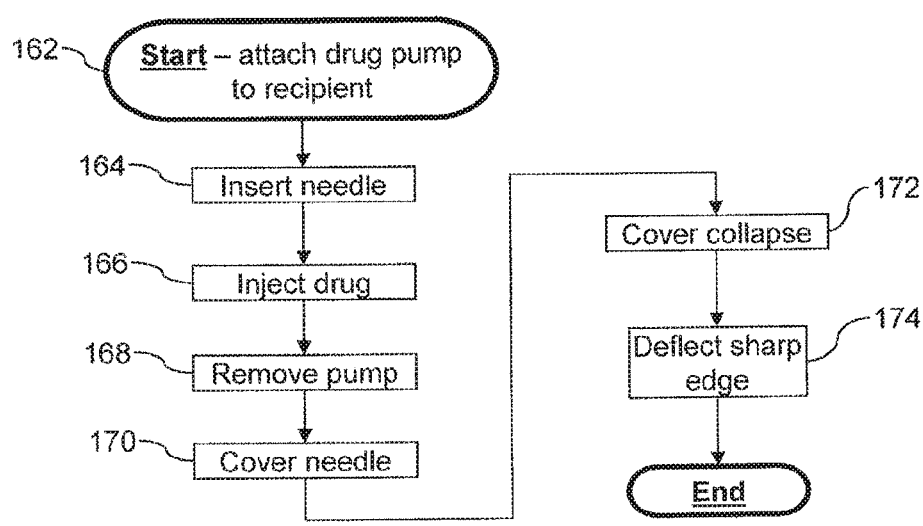
FIG. 1a is a flow chart illustrating an exemplary method according to the current invention.

The present invention, in some embodiments thereof, relates to a system and method for preventing a reexposure of point of a needle by deflecting the point and more particularly, but not exclusively, to a guide and/or a safety clip for deflecting and/or enclosing the point upon collapse of a needle protector flap.

A portable drug pump may include a protective flap for covering a protruding needle. Under certain conditions, the protective flap may collapse, reexposing the needle. In some embodiments, the present invention may include an optional guide for deflecting the needle to a secure space thereby preventing reexposure of the needle in the event of collapse of the flap. An optional enclosure may shield the secure space.

In some embodiments, in a protecting position, when the flap is in the protecting position, the guide may be disposed at an incline to the needle. The angle of include between the deflective guide and the needle may determine the direction to which the point will be deflected upon collapse of the flap. The angle between the needle and the deflective guide may optionally range between 5° to 85°. The guide may take a form of a flat plate and/or the guide may include walls and/or a channel for directing the needle tip to the secure space and/or the guide may have a concave form for directing the needle tip.

In some embodiments, deflecting the point will include bending a needle. Additionally or alternatively, deflecting the point may include pivoting the needle and/or causing a translation of the support of the needle.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

FIG. 1a is a flow chart illustrating a simplified example of a method for preventing reexposure of a point when a protecting flap is subject to a collapse failure. Such a failure may result, for example, from a strong blow to the flap.

An injection apparatus may be used, for example, by a patient who needs to receive a drug by subcutaneous injection. The patient may prefer to receive the injection at home using the injection apparatus rather than traveling to a doctor. The recipient may wear the injector by optionally attaching 162 the apparatus to his body. Attachment 162 may be, for example, by means of an adhesive on the base of the injector.

In some embodiments, after attachment 162 the injector may optionally insert 164 a hypodermic needle subcutaneously into the recipient. The injection apparatus may then optionally inject 166 the drug through the needle into the recipient. After injection 166, the patient optionally removes 168 the injection apparatus.

In some embodiments, after removal 168, the needle will remain protruding from the injection apparatus, presenting a needle stick hazard. In order to protect people from the needle, the injection apparatus may optionally include a protective flap for covering 170 the needle.

When the flap is in a protecting position, at times, a strong force may collapse 172 the protecting flap. For example, the patient may throw the apparatus into the garbage and then later compact the garbage with his foot. The compaction force may collapse the protective flap of the injection apparatus, possibly reexposing the sharp tip of the needle.

In some embodiments, the flap may include an optional fail-safe guide to prevent reexposure of the needle in the event of collapse 172 of the flap. The guide may optionally deflect 174 a point of a needle into a secure space, reducing the likelihood of a needle stick injury.

Figure 1B:
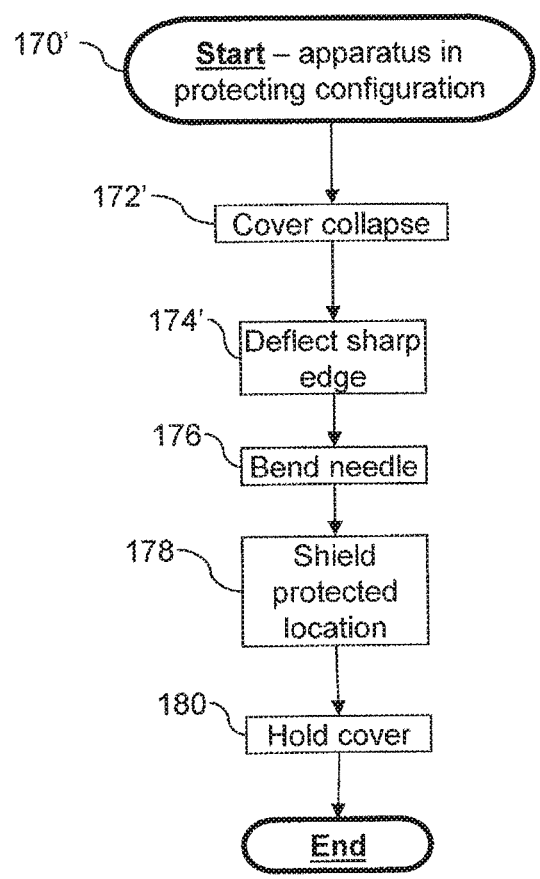
FIG. 1b is a flow chart illustrating an exemplary method according to the current invention including extra optional steps.

FIG. 1b is a flow chart illustrating a method of averting a needle stick including optional steps. A method of averting needle sticks may include one, some or all of the optional steps.

An injection apparatus is supplied in a protecting 170' position wherein a needle protecting flap covers the point.

When a strong force collapsed 172' the protecting flap, the point is optionally deflected 174' into a secure space.

In the exemplary embodiment of FIG. 1b, the point may optionally be on a tip of a needle. The needle may optionally be bent 176 during deflection 174'. Alternatively or additionally, the needle may be mounted on a movable support and the needle may pivot and/or translate while the point is being deflected 174'.

In some cases, a shield (for example a clip) may be included in the injector for shielding 178 the secure space. Shielding 178 the secure space may prevent needle sticks, for example, when the flap breaks and/or a person pushes his finger under the flap and/or when the displacement of the flap uncovers the needle and/or when the point is displaced away from under the flap by bending and/or pivoting and/or translating. Alternatively or additionally, the needle and/or the guide and/or the clip may hold 180 the needle protective flap in a closed position, thereby shielding 178 the needle with the flap.

Figure 2A:
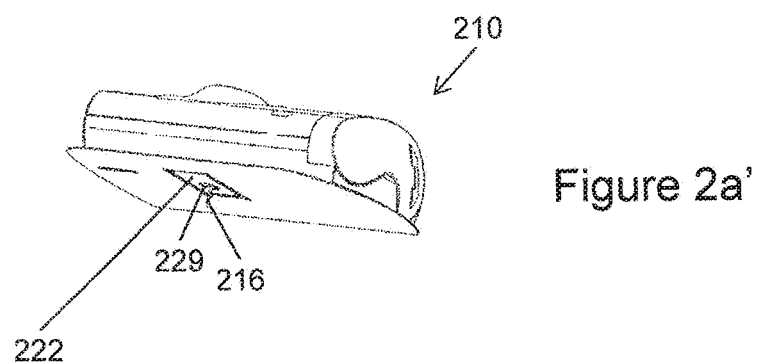
FIG. 2a is a simplified cutaway illustration of an exemplary embodiment drug pump attached to a recipient with a flap in an exposing position.

FIGS. 2a, 2a', 2b, 2c, 2c', 2d, 3a, 3b, 3c, 3d, 3d', 4 and 4' are views of an exemplary embodiment 210 of a portable drug injector apparatus and a needle protection flap 222. In embodiment 210, flap 222 is optionally pivotally mounted to a base of the apparatus housing.

Figure 2B:
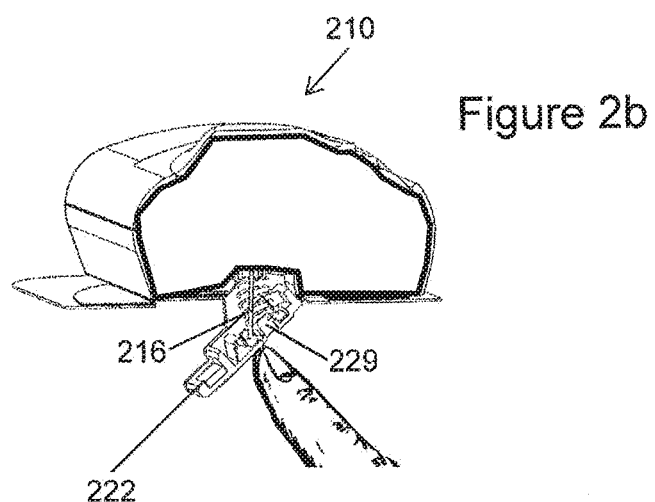
FIG. 2b is a perspective view of the embodiment of FIG. 2a with the flap in a protecting position.

FIGS. 2a-c are a simplified illustration of a needle protector in various positions. Particularly, FIGS. 2a, a' illustrate the injector and flap in an exposing position, wherein needle 216 is exposed. For example, in FIG. 2a, flap 222 is shown in the exposing position while the apparatus is injecting a drug into a flesh 205 of a recipient. FIG. 2b illustrates the injector in a protecting position. FIGS. 2c, c' illustrate the injector after collapse of protective flap 222. Particularly, FIG. 2c' illustrates a secure space 256 and a guide 252 for deflecting a point 232 of needle 216 into the secure space. FIG. 2 also shows an optional clip 254 shielding secure space 256.

FIG. 2a, a' illustrates protective flap 222 in an exposing position (for example while injecting a drug into a patient). In FIG. 2a, the embodiment 210 is shown attached to a recipient. Needle 216 projects out of a needle opening 229 in flap 222 and is inserted into flesh 205. During injection, the base of the injector is typically held against the skin of the recipient by an adhesive. In the exposing position, flap 222 is optionally held flush to the base of the injector housing by pressure against skin of the recipient. Needle 216 is optionally locked in the protruding position. The drug may be administered to the recipient, for example, via needle 216 and/or a cannula.

Embodiments of the invention are described with reference to a needle alone, but apply as well to a needle disposed in a cannula or any other delivery device. The term "needle" is used throughout the specification and claims to encompass all such delivery devices and/or sharp implements.

Embodiment 210 typically includes a motor, a battery and a control unit (all not shown) within the housing of the apparatus. After needle 216 has penetrated the skin of the patient, the control unit controls operation of the motor to administer a controlled amount of the substance to the patient at a controlled rate of delivery. Of course, the needle assembly of the present invention can be used in other applications and does not have to be used with a controlled motorized delivery system.

When injection has finished the injector is lifted away from the skin of the recipient and flap 222 pivots away from the base of the apparatus to a protecting position as illustrated, for example, in FIG. 2b (and in more detail in FIGS. 3a-c). In the protecting position, flap 222 covers the point of needle 216 protecting from a needle stick hazard.

There is a concern that if flap 222 is pivoted back toward the injector housing with a force sufficient to bend needle 216, then point 232 may be reexposed creating a needle stick hazard. For example, in FIGS. 2b and 2c if needle 216 were bent leftward toward the open space between flap 222 and the housing base without any protective mechanism a person could get stuck if he pushed his fingers under the flap, as shown in FIG. 2c. Embodiment 210 includes a guide and clip to deflect and shield needle 216 and prevent such needle sticks as illustrated, for example, in FIG. 2c'.

FIG. 2c' is an expanded cutaway illustration of the exemplary embodiment of flap 222. Particularly, FIG. 2c' illustrates an optional guide 252 and an optional clip 254 and an optional secure space 256, which prevent reexposure of needle 216 in the event of collapsing of flap 222. Particularly, upon collapse of flap 222, guide 252 pushes needle 216 into secure space 256. Optionally, clip 254 shields secure space 256. (See below more detailed discussion of the exemplary embodiment of guide 252, clip 254, and space 252 in reference to FIGS. 4 and 4'.)

Figure 2D:
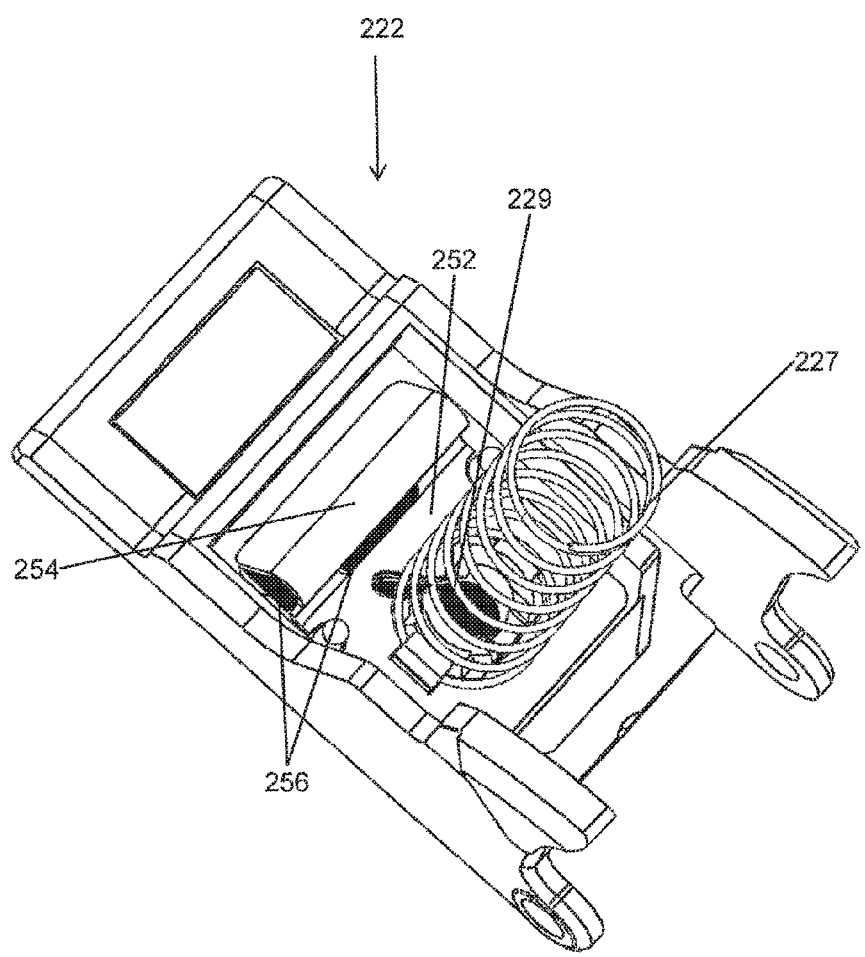
FIG. 2d is a perspective view of the flap.

FIG. 2d shows a perspective view of flap 222.

In FIGS. 3a-c, embodiment 210 is shown in the protecting position. After finishing the drug administration, embodiment 210 is typically lifted off the recipient's body. As the injector is lifted, biasing device 227 to pushes flap 222 away from the base of the apparatus. Flap 222 pivots into the protecting position. In FIGS. 3a-c, flap 222 is shown in the protecting position, covering point 232.

As illustrated, for example, in FIG. 3c, as flap 222 moves from the exposing position (FIGS. 2a, a') into the protecting position (FIGS. 2b, 3a-c), a needle opening 229 optionally follows a curved trajectory 330 (downward and rightward in FIG. 3c). As opening 229 moves along trajectory 330, needle 216 is optionally flexed elastically rightward. When opening 229 passes below point 232, needle 216 optionally snaps back leftward to its un-stressed shape. As illustrated, for example, in FIG. 3c, in its unstressed shape, needle 216 optionally remains locked protruding out of the housing. Needle 216 is no longer aligned with needle opening 229. Needle 216 optionally serves as a prop, preventing flap 222 from returning to the exposing position. Flap 222 serves as a protector blocking point 232.

Figure 3D:
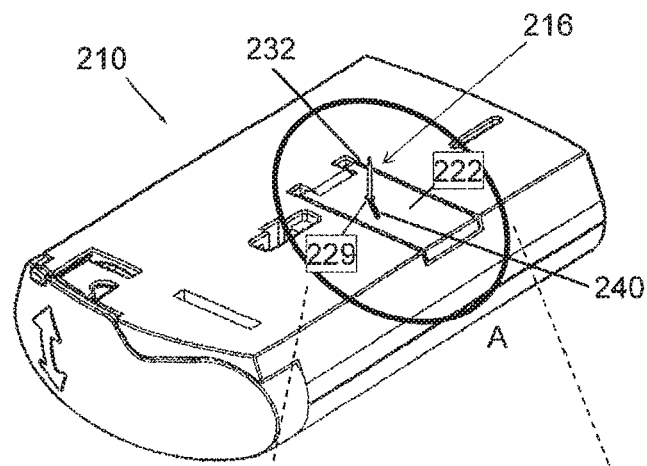
FIG. 3d is a perspective view of the base of the apparatus of FIGS. 2a-d, FIGS. 3a-c with the flap in the exposing position showing the form of the needle opening.
Figure 3D:
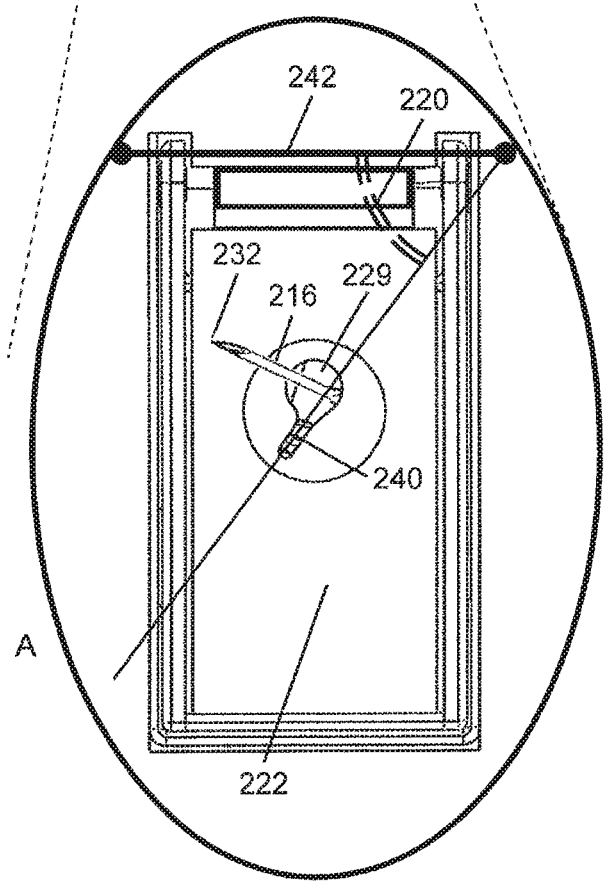

In FIG. 3d, d', it is seen that, in exemplary embodiment 210, opening 229 is optionally non-circular. In some embodiments, the form of needle opening 229 may be selected to adjust resistance to pivoting of flap 222 from the exposing position (FIGS. 2a, a', 3d, d') to the protecting position (FIGS. 3a-c). Additionally or alternatively, the form of needle opening 229 may be selected to adjust stability of flap 222 in the protecting position.

In embodiment 210, opening 229 optionally includes a linear duct 240. In embodiment 210, duct 240 is optionally directed at an angle 220 of approximately 55° with a pivoting axis 242 of flap 222.

In exemplary embodiment 210, as flap 222 pivots from the exposing position (for example, as illustrated in FIG. 2a, a', 3d, d') into the protecting position (for example, as illustrated in FIGS. 3a-c), needle 216 slides along duct 240 flexing to remain in opening 229. Once flap 222 has pivoted far enough, point 232 passes through opening 229 and needle 216 returns to its un-stressed shape (as illustrated, for example, in FIG. 3c).

In embodiment 210, the resistance of flap 222 to pivoting may increase as the required flexing of needle 216 increases. The flexing required of needle 216 may depend on the length and angle 220 of duct 240. Generally, the resistance may decrease as angle 220 increases from 0° to 90°.

In the protected mode of embodiment 210 (FIG. 3*a-c*), as long as point 232 is not aligned with opening 229, needle 216 acts as a prop to stabilize flap 222. The likelihood that point 232 will unintentionally realign with opening 229 may increase as angle 220 increases from 0° to 90°.

Optionally, angle 220 may range between 5° and 85°. In many embodiments, angle 220 may range between 40° and 80°. In some embodiments, duct 240 may be curved and/or have a non-uniform width. Optionally opening 229 may have a different form. More generally, the flexing required of needle 216 may depend on the angle and distance between the un-stressed location of needle 216 and the contact point between needle 216 and opening 229 at the point of maximum flexing. More generally, the likelihood of unintentional alignment, in the protecting position, between needle 216 and opening 229 may depend on the distance between the unstressed location of point 232 and the closest edge of opening 229, in the protecting position.

FIG. 3*c* illustrates an exemplary embodiment of an optional guide 252 and an optional enclosure, safety clip 254. Guide 252 is optionally integrated into flap 222. For example, guide 252 may be attached to flap 222 and/or it may be integral to flap 222.

Under some conditions flap 222 may collapse. For example, a strong force may cause flap 222 to collapse and pivot towards the base of the apparatus. As flap 222 pivots, guide 252 deflects point 232 into a secure space 256 of clip 254 (as shown in FIGS. 4 and 4'), preventing a needle stick hazard.

In some embodiments, clip 254 optionally shields secure space 256. Additionally or alternatively, clip 254 may clasp point 232.

In the protecting position of FIG. 3*a-c*, guide 252 is optionally disposed at an approximately 45° angle 318 to the axis of needle 216 and point 232. In some embodiments, guide may be disposed at an angle 318 ranging between 5° and 85° to point 232.

Figure 4:
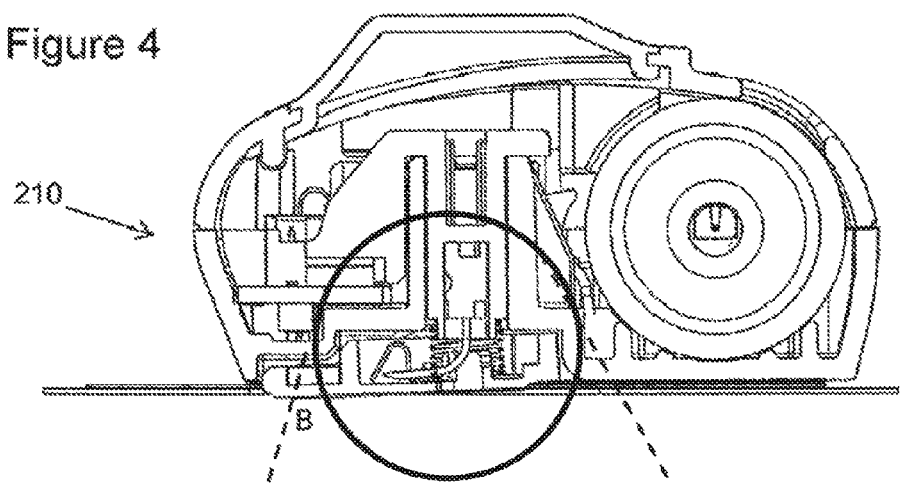
FIG. 4 is a cutaway view of the embodiment of FIGS. 2a-d, 3a-d after collapse of the protective flap.
Figure 4:
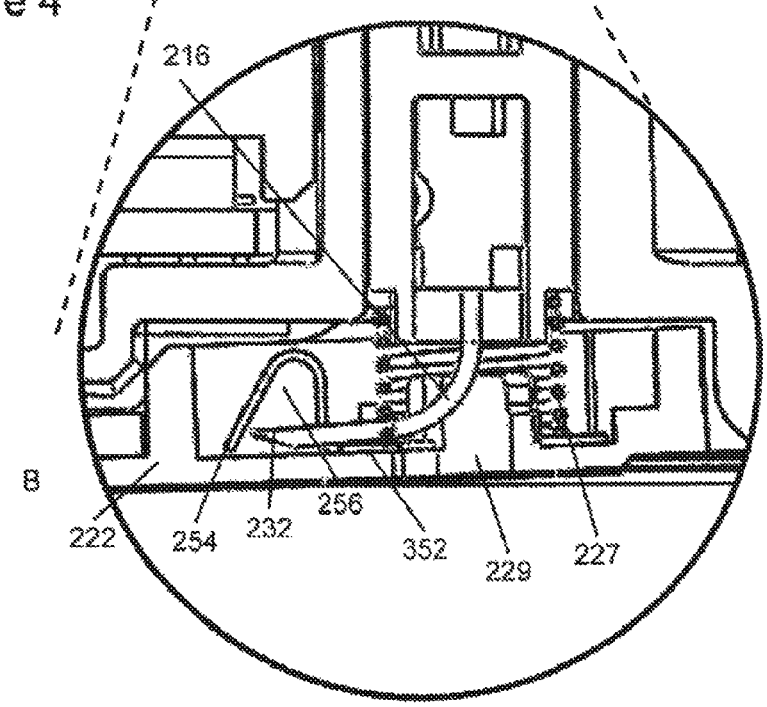

FIG. 4 shows embodiment 210 in after collapse of flap 222. FIG. 4' shows an enlarged view of circle B. In FIGS. 4, and 4' guide 252 has deflected point 232 into protected secure space 256. In embodiment 210, guide 252 is optionally configured so that deflection is in the direction away from the joint between flap 222 and the injector housing. In alternative embodiments, the needle may be defected towards the joint and/or at an angle to the pivoting connection.

In some embodiments, Clip 254 may be optionally configured to clasp bent needle 216 thereby securing protective flap 222 in a closed position. In the closed position, flap 222 may shield point 232. In some embodiments clip 254 may retain point 232 inside of secure space 256. For example, clip 254 may grasp needle 216 and/or point 232 (with a clasping force). Alternatively or additionally clip 254 may enclose and shield point 232 but not grasp needle 216 or point 232.

The composition of clip 254 and/or guide 252 may include plastic, metal, paper, wood and/or another suitable material.

Figure 5A:
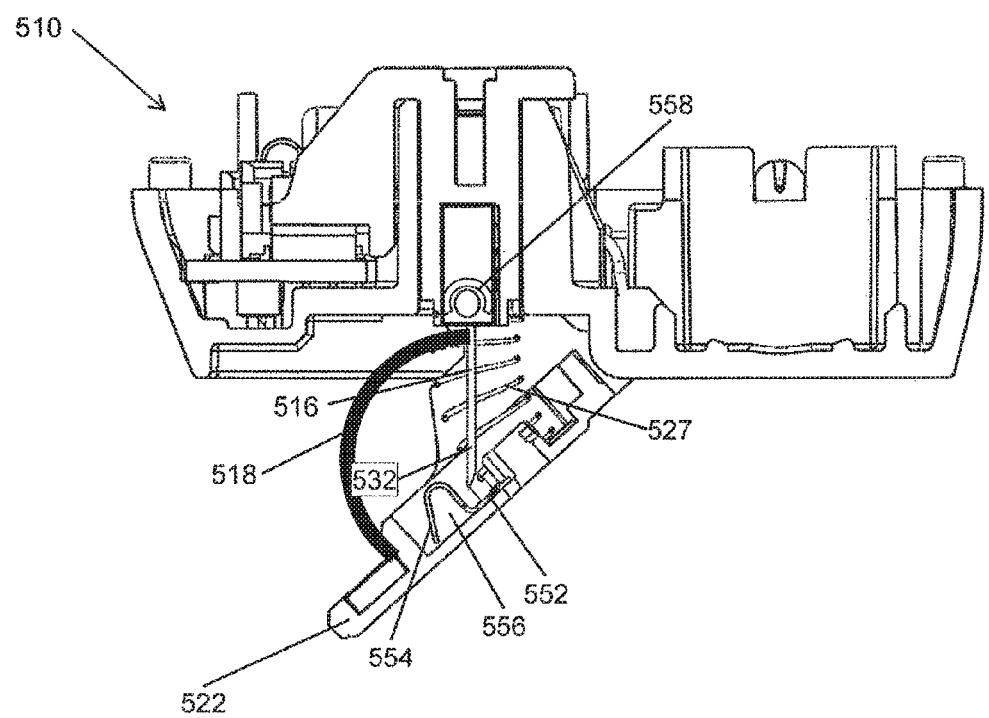
FIG. 5a is a cutaway view of an additional embodiment of an injector with a flap in a protecting position.

FIG. 5*a,b* illustrate another exemplary embodiment 510 of an apparatus. In embodiment 510, upon collapse of an optional protective flap 522, a needle 516 pivots into a secure space 556.

Figure 5B:
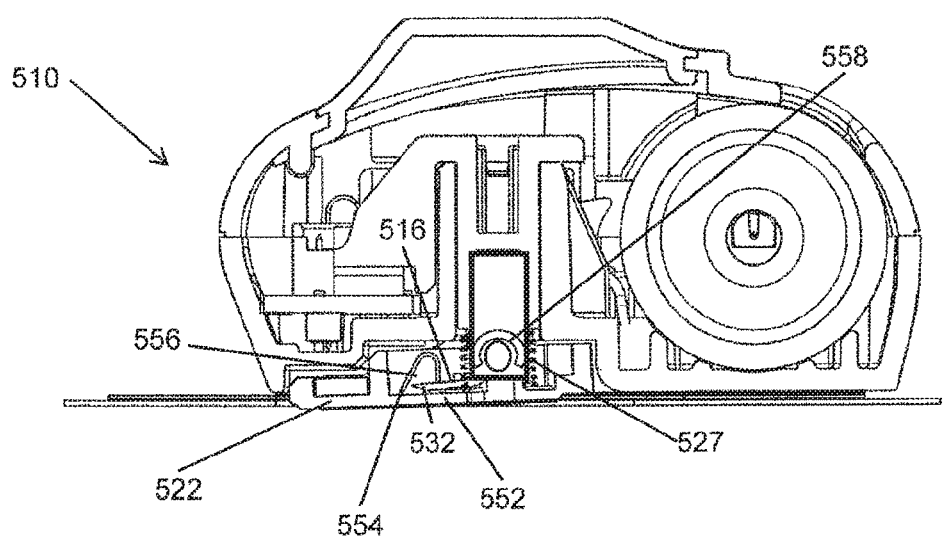
FIG. 5b is a cutaway view of the embodiment of FIG. 5a after collapse of the flap.

In embodiment 510, needle 516 is optionally mounted on a pivoting support 558. FIG. 5*a* shows embodiment 510 in a protecting position. FIG. 5*b* shows embodiment 510 after collapse of flap 522.

In FIG. 5*a*, a point 532 is covered by flap 522. An optional guide 552 is optionally inclined at an angle 518 with respect to point 532. Flap 522 is held in the protecting position by an optional biasing device 527 and by needle 516.

Under some conditions flap 522 may be forced to pivot back towards the base of the apparatus. As flap 522 pivots toward the base of the apparatus, guide 552 deflects point 532 into a secure space 556. At first, pivoting support 558 allows needle 516 to pivot without bending. As flap 522 collapses further, point 532 collides with the back side of an optional clip 554 forcing needle 516 to bend as shown in FIG. 5*b*.

FIGS. 6*a,b* illustrate another exemplary embodiment 610 of an apparatus having fail-safe needle protection according to the current invention. Optionally, in embodiment 610, upon collapse of flap 622, point 632 is deflected into a secure space 656 formed at the joint between flap 622 and the housing of the apparatus.

In FIGS. 6*a,b*, a needle 616 is mounted on an optional sliding pivoting support 658.

Pivoting and translating of support 658 allows a point 632 to be deflected into secure space 656 without bending needle 616.

Figure 6B:
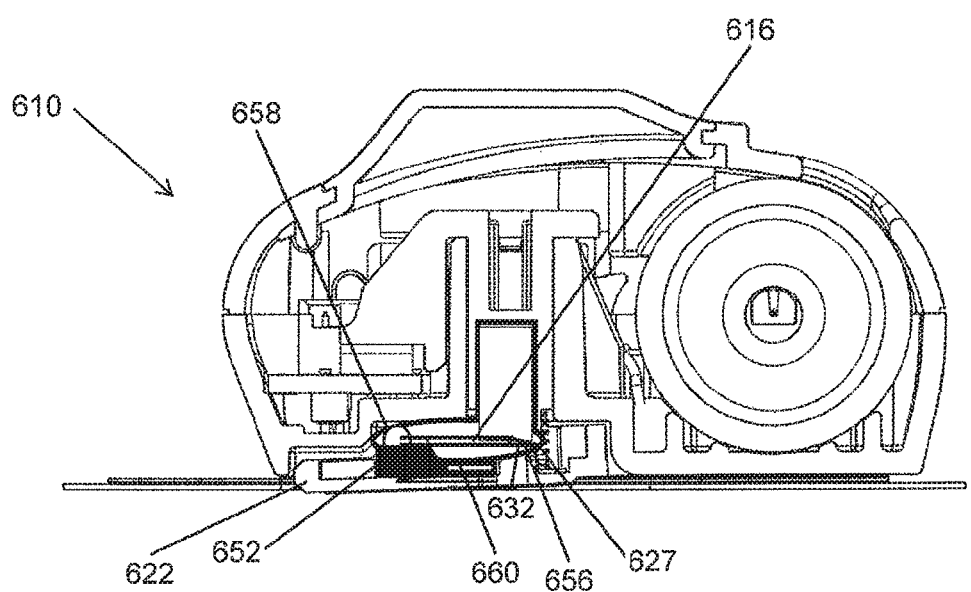
FIG. 6b is a cutaway view of the embodiment of FIG. 6a after collapse of the flap.

FIG. 6*a* shows embodiment 610 in a protecting position. FIG. 6*b* shows embodiment 610 after collapse of an optional protective flap 622.

In FIG. 6*a*, a point 632 is covered by flap 622. Flap 622 is held in a protecting position by an optimal biasing device 627 and by needle 616. An optional guide 652 is optionally held inclined at an angle 618 with respect to point 632. In embodiment 610, the inclination of guide 652 is optionally opposite that of flap 622.

Flap 622 may sometimes be forced to pivot back towards the base of the apparatus. As flap 622 pivots toward the base of the apparatus, guide 652 deflects point 632 away from the opening between flap 622 and the base of the apparatus. Point 632 is deflected towards secure space 656 formed by the joint between flap 622 and the housing base. Support 658 optionally pivots and translates along an optional track 660 allowing needle 616 to pivot towards secure space 656. As flap 622 continues to collapse, point 632 is pushed by guide 652. Eventually, needle 616 pivots without bending until it lies flat up against guide 652 parallel to the base of the apparatus. In FIG. 6*b*, point 632 is located in secure space 656 shielded by the base of the apparatus and flap 622.

Figure 7:
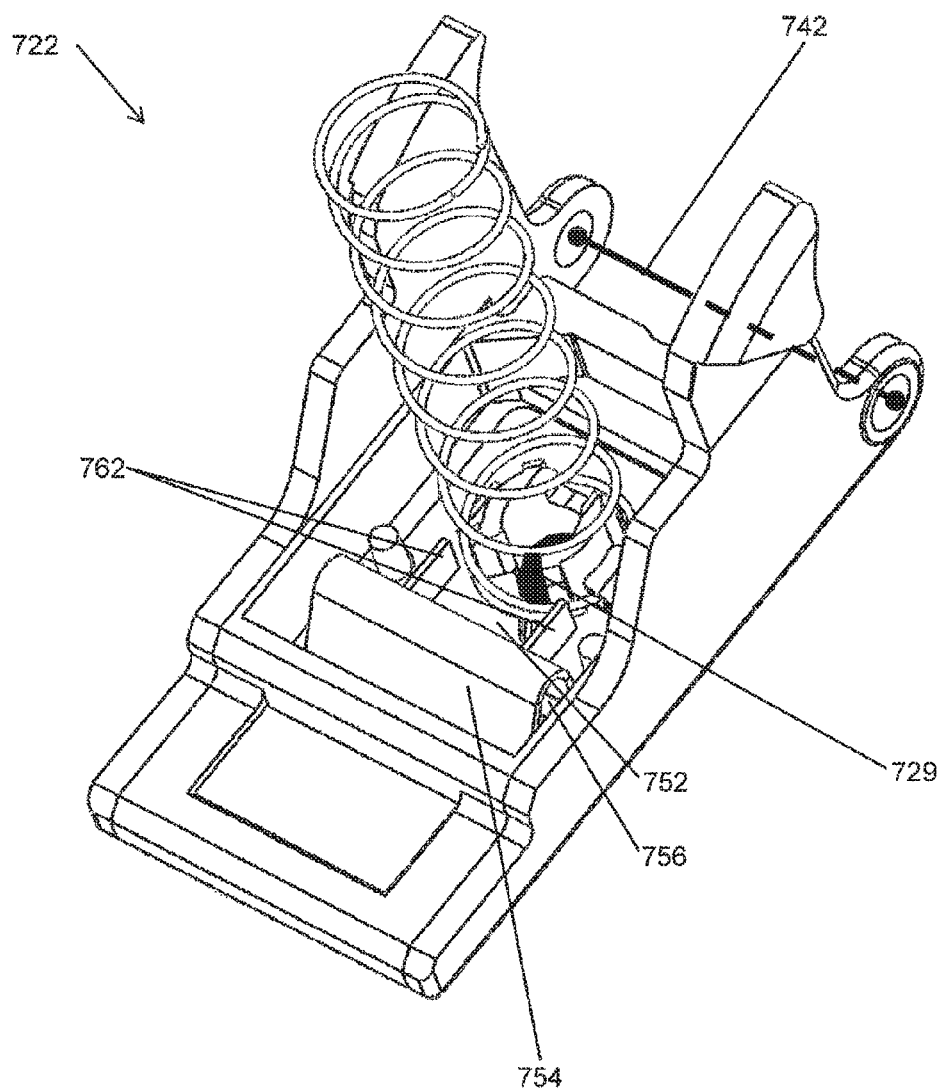
FIG. 7 is a perspective view of a further alternative embodiment of a flap.

FIG. 7 is a close up perspective view of a further exemplary embodiment of a protective flap 722. Visible in the drawing are exemplary embodiments of a pivoting axis 742 and a needle opening 729 and a guide 752 and a shielding clip 754 and a secure space 756 and a biasing element 727. Embodiment 722 also includes barriers 762 forming a channel for preventing a needle from twisting sideward during a collapse of flap 722.

Figure 8:
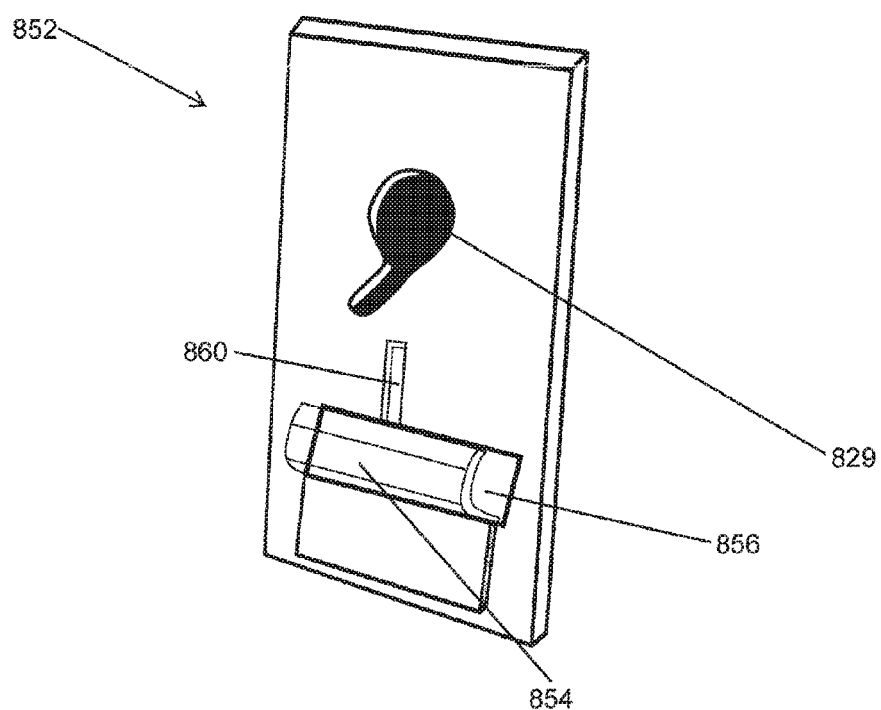
FIG. 8 is a perspective view of a further alternative embodiment of a guide.

FIG. 8 is a close up perspective view of an exemplary embodiment of a guide 852. Visible in the drawing are exemplary embodiments of a needle opening 829 and a shielding clip 854 and a secure space 856 and a channel 860 for directing the a needle point to secure space 856 and/or for preventing a needle from twisting sideward during a collapse of a protecting flap. Alternatively or additionally channel 860 may have a non-rectangular shape (for example, it could have a wedge shape). Alternatively or additionally channel 860 could have a non-rectangular cross-section (for example it could have a V shaped cross section). Alternatively or additionally, channel 860 could be formed by a concave shape of guide 856.

It is expected that during the life of a patent maturing from this application many relevant technologies will be developed and the scope of the terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An injection apparatus wearable by a recipient for delivering a drug to the recipient, the injection apparatus comprising:
   a housing having a base, the base engaging skin of the recipient during injection;
   a generally linear needle having a needle point projecting from the housing;
   a flap pivotably mounted to the base of the housing, the flap including a bottom wall and a clip extending therefrom, a secure space located between the clip and bottom wall, the flap having:
      an exposed position, generally co-planar with the base, wherein at least the needle point is aligned with and protrudes through an aperture in the flap,
      a protecting position, wherein the flap is pivoted away from the exposed position in a direction away from the base of the housing and covers the needle point, such and the needle point is positioned between said flap and said base and is not aligned with the aperture, and
      a collapsed position, wherein the flap is pivoted toward the base of the housing from the protecting position;
   wherein upon pivoting of the flap from the protecting position to the collapsed position, the flap deflects the needle point into the secure space within the flap while bending the needle to a non-linear orientation, thereby preventing re-exposure of the needle point beyond the flap.

2. The injection apparatus of claim 1, further comprising a guide attached to the flap, the guide being positioned relative to the needle point such that upon pivoting of the flap from the protecting position to the collapsed position, the guide deflects the needle point into the secure space within the flap.

3. The injection apparatus of claim 2, wherein the guide is integrated into the flap.

4. The injection apparatus of claim 2, wherein the guide comprises one of a plate, oriented at an incline to the needle point in the protecting position of the flap, or a concave plate within the flap, for deflecting the needle point into the secure space within the flap.

5. The injection apparatus of claim 1, further comprising a biasing device positioned between the flap and the housing for moving the flap from the exposed position to the protecting position.

6. The injection apparatus of claim 1, wherein movement of the flap from the exposed position to the protecting position elastically flexes the needle out of the aperture.

7. The injection apparatus of claim 1, wherein the aperture is non-circular.

8. The injection apparatus of claim 7, wherein the aperture includes a linear duct.

9. The injection apparatus of claim 8, wherein upon movement of the flap from the exposed position to the protecting position, the needle initially slides along the duct prior to retracting from the aperture and misaligning therewith.

* * * * *